(12) United States Patent
Gosselin et al.

(10) Patent No.: US 12,029,819 B2
(45) Date of Patent: *Jul. 9, 2024

(54) PHARMACEUTICAL COMPOSITIONS COMPRISING LONAFARNIB AND RITONAVIR

(71) Applicant: Eiger BioPharmaceuticals, Inc., Palo Alto, CA (US)

(72) Inventors: Patrick Gosselin, Palo Alto, CA (US); Aimesther Betancourt, Palo Alto, CA (US)

(73) Assignee: Eiger BioPharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/969,005

(22) Filed: Oct. 19, 2022

(65) Prior Publication Data

US 2023/0218530 A1 Jul. 13, 2023

Related U.S. Application Data

(63) Continuation of application No. 17/073,920, filed on Oct. 19, 2020, now Pat. No. 11,517,532, which is a continuation of application No. 15/567,444, filed as application No. PCT/US2016/028651 on Apr. 21, 2016, now Pat. No. 10,835,496.

(60) Provisional application No. 62/153,815, filed on Apr. 28, 2015, provisional application No. 62/150,721, filed on Apr. 21, 2015.

(51) Int. Cl.
| | |
|---|---|
| *A61K 9/14* | (2006.01) |
| *A61K 31/427* | (2006.01) |
| *A61K 31/4545* | (2006.01) |
| *A61K 47/32* | (2006.01) |
| *A61K 47/38* | (2006.01) |
| *A61P 31/14* | (2006.01) |

(52) U.S. Cl.
CPC ............ *A61K 9/146* (2013.01); *A61K 31/427* (2013.01); *A61K 31/4545* (2013.01); *A61K 47/32* (2013.01); *A61K 47/38* (2013.01); *A61P 31/14* (2018.01)

(58) Field of Classification Search
CPC .. A61K 31/427; A61K 31/4545; A61K 47/32; A61K 47/38; A61K 9/146; A61P 31/14
See application file for complete search history.

(56) References Cited

U.S. PATENT DOCUMENTS

| | | | |
|---|---|---|---|
| 4,695,623 A | 9/1987 | Stabinsky | |
| 4,897,471 A | 1/1990 | Stabinsky | |
| 5,382,657 A | 1/1995 | Karasiewicz et al. | |
| 5,541,206 A | 7/1996 | Kempf et al. | |
| 5,648,497 A | 7/1997 | Kempf et al. | |
| 5,951,974 A | 9/1999 | Gilbert et al. | |
| 5,981,709 A | 11/1999 | Greenwald et al. | |
| 6,169,096 B1 | 1/2001 | Venet et al. | |
| 6,365,600 B1 | 4/2002 | End et al. | |
| 6,420,387 B1 | 7/2002 | Venet et al. | |
| 6,627,223 B2 | 9/2003 | Percel et al. | |
| 6,734,194 B2 | 5/2004 | End et al. | |
| 6,743,805 B2 | 6/2004 | End et al. | |
| 6,838,467 B2 | 1/2005 | End | |
| 6,927,040 B2 | 8/2005 | Sheppard et al. | |
| 7,038,032 B2 | 5/2006 | Sheppard et al. | |
| 7,135,170 B2 | 11/2006 | Klucher et al. | |
| 7,148,459 B2 | 12/2006 | Williford et al. | |
| 7,157,559 B2 | 1/2007 | Brady et al. | |
| 7,183,416 B2 | 2/2007 | Chemburkar et al. | |
| 7,253,183 B2 | 8/2007 | End et al. | |
| 7,364,752 B1 | 4/2008 | Fort et al. | |
| 7,511,027 B2 | 3/2009 | Casey et al. | |
| 7,595,174 B2 | 9/2009 | Brady et al. | |
| 7,759,092 B2 | 7/2010 | Zamost et al. | |
| 7,968,315 B2 | 6/2011 | Zamost et al. | |
| 8,211,670 B2 | 7/2012 | Zamost et al. | |
| 8,293,726 B2 | 10/2012 | Habib | |
| 8,759,027 B2 | 6/2014 | Zamost et al. | |
| 8,980,245 B2 | 3/2015 | Ho | |
| 9,096,556 B2 | 8/2015 | Reddy et al. | |
| 10,076,512 B2 | 9/2018 | Cory et al. | |
| 10,828,283 B2 | 11/2020 | Cory et al. | |
| 10,835,496 B2 | 11/2020 | Gosselin et al. | |
| 11,311,519 B2 | 4/2022 | Cory et al. | |
| 11,517,532 B2 * | 12/2022 | Gosselin | A61K 9/146 |

(Continued)

FOREIGN PATENT DOCUMENTS

| | | |
|---|---|---|
| JP | 2002-533435 A | 10/2002 |
| JP | 2004-501153 A | 1/2004 |

(Continued)

OTHER PUBLICATIONS

Abbas, Z., et al., "Management of Hepatitis Delta: Need for Novel Therapeutic Options", World Journal of Gastroenterology, vol. 21, No. 32. Aug. 28, 2015, p. 9461-9465, DOI:10.3748/wjg.v21.i32.9461.

Andric, N. "Remote consultation referral system: An effective way to treat homeless and marginalized patients with chronic hepatitis C in primary care", Hepatitis-Viral. Journal of Gastroenterology and Hepatology, vol. 32, Issue S2: (2017) p. 65-86. doi: 10.1111/jgh.13892.

Bedossa, P., et al., "Intraobserver and Interobserver Variations in Liver Biopsy Interpretation in Patients with Chronic Hepatitis C", Hepatology, vol. 20, Issue 1, Jul. 1994, p. 15-20, DOI:https://doi.org/10.1002/hep.1840200104.

(Continued)

*Primary Examiner* — Kara R McMillian
(74) *Attorney, Agent, or Firm* — Kilpatrick Townsend & Stockton LLP

(57) ABSTRACT

Lonafarnib and ritonavir, or a pharmaceutically acceptable salt thereof, are used in combination to treat HDV infection. In one aspect, amorphous co-precipitates comprising lonafarnib, ritonavir, and a co-polymer are provided.

20 Claims, 11 Drawing Sheets

(56) References Cited

U.S. PATENT DOCUMENTS

| | | |
|---|---|---|
| 11,793,793 B2 | 10/2023 | Cory et al. |
| 2003/0096014 A1 | 5/2003 | Sherman |
| 2003/0114471 A1 | 6/2003 | Venet et al. |
| 2003/0181355 A1 | 9/2003 | Glenn |
| 2005/0136115 A1 | 6/2005 | Kulkarni et al. |
| 2006/0111398 A1 | 5/2006 | Fourie |
| 2007/0287664 A1 | 12/2007 | Ralston et al. |
| 2008/0021078 A1 | 1/2008 | Tidmarsh et al. |
| 2009/0142393 A1 | 6/2009 | Xu et al. |
| 2010/0029667 A1 | 2/2010 | Ketner et al. |
| 2011/0105557 A1 | 5/2011 | End |
| 2011/0313009 A1 | 12/2011 | Tidmarsh et al. |
| 2013/0102526 A1 | 4/2013 | Bernstein et al. |
| 2013/0165371 A1 | 6/2013 | Dobry et al. |
| 2013/0193598 A1 | 8/2013 | Friesen et al. |
| 2014/0017314 A1 | 1/2014 | Beyerinck et al. |
| 2014/0178333 A1 | 6/2014 | Brady et al. |
| 2014/0210117 A1 | 7/2014 | Friesen et al. |
| 2014/0220141 A1 | 8/2014 | Giardiello et al. |
| 2015/0028503 A1 | 1/2015 | Beyerinck et al. |
| 2015/0273354 A1 | 10/2015 | Dobry et al. |
| 2015/0374827 A1 | 12/2015 | Miller et al. |
| 2017/0042862 A1 | 2/2017 | Cory et al. |
| 2018/0110734 A1 | 4/2018 | Gosselin et al. |
| 2018/0338993 A1 | 11/2018 | Cory et al. |
| 2019/0111110 A1 | 4/2019 | Martins |
| 2019/0167646 A1 | 6/2019 | Cory et al. |
| 2020/0375955 A1 | 12/2020 | Cory et al. |
| 2023/0046607 A1* | 2/2023 | Cory ................ A61P 31/00 |

FOREIGN PATENT DOCUMENTS

| | | |
|---|---|---|
| JP | 2004-510762 A | 4/2004 |
| JP | 2009-530382 A | 8/2009 |
| JP | 2012-111775 A | 6/2012 |
| JP | 2012-524753 A | 10/2012 |
| JP | 2014-509630 A | 4/2014 |
| JP | 2014-523878 A | 9/2014 |
| JP | 2014-530874 A | 11/2014 |
| WO | 97-01349 A1 | 1/1997 |
| WO | 97-23478 A1 | 7/1997 |
| WO | 97-31641 A1 | 9/1997 |
| WO | 00-39082 A2 | 7/2000 |
| WO | 2005-097165 A2 | 10/2005 |
| WO | 2005-117864 A1 | 12/2005 |
| WO | 2007-012033 A2 | 1/2007 |
| WO | 2007-013944 A2 | 2/2007 |
| WO | 2007-041713 A1 | 4/2007 |
| WO | 2008-137692 A1 | 11/2008 |
| WO | 2009-042960 A1 | 4/2009 |
| WO | 2011-088126 A2 | 7/2011 |
| WO | 2012-131061 A1 | 10/2012 |
| WO | 2012-164575 A2 | 12/2012 |
| WO | 2012-174220 A1 | 12/2012 |
| WO | 2013-024494 A2 | 2/2013 |
| WO | 2013-034927 A1 | 3/2013 |
| WO | 2013-059638 A1 | 4/2013 |
| WO | 2013-116720 A1 | 8/2013 |
| WO | 2014-071231 A1 | 5/2014 |
| WO | 2015-168648 A1 | 11/2015 |
| WO | 2016-090107 A2 | 6/2016 |
| WO | 2016-172342 A1 | 10/2016 |
| WO | 2017-079009 A1 | 5/2017 |
| WO | 2020-041778 A1 | 2/2020 |

OTHER PUBLICATIONS

Bergmeyer, H.U., et al. "Approved recommendation (1985) on IFCC methods for the measurement of catalytic concentration of enzymes", J. Clin. Chem. Clin. Biochem., vol. 24, No. 7, Jan. 1986, p. 481-495.

Blanchet, M., et al., "Use of FDA approved therapeutics with hNTCP metabolic inhibitory properties to impair the HDV lifecycle", Antiviral Research, Elsevier Masson, vol. 106, year 2014, p. 111-115, DOI:http://dx.doi.org/10.1016/j.antiviral.2014.03.017.

Bordier, B.B., et al. "A prenylation inhibitor prevents production of infectious hepatitis delta virus particles", J. Virol., vol. 76, Issue 20, Oct. 2002, p. 10465-10472, DOI:10.1128/jvi.76.20.10465-10472.2002.

Bordier, B.B., et al., "In vivo antiviral efficacy of prenylation inhibitors against hepatitis delta virus", The Journal of Clinical Investigation, vol. 112, No. 3, Aug. 1, 2003, p. 407-414, DOI:10.1172/JCI200317704.

Brunt, E., "Grading and staging the histopathological lesions of chronic hepatitis: The Knodell histology activity index and beyond" Hepatology, vol. 31, Issue 1, Dec. 30, 2003, p. 241-246, DOI:https://doi.org/10.1002/hep.510310136.

Canini, L., et al., "Understanding hepatitis delta virus dynamics and antiviral efficacy of the prenylation inhibitor lonafarnib", AASLD Abstracts, Hepatology, vol. 60, No. 4, Oct. 2014, p. 317A-321A.

Chudy, M., et al. "Collaborative study to establish a World Health Organization international standard for hepatitis D virus RNA for nucleic acid amplification technique (NAT)-based assays", World Health Organization, Oct. 2013, 29 pages.

Erba, H.P., et al. "Four different regimens of farnesyltransferase inhibitor tipifarnib in older, untreated acute myeloid leukemia patients: North American Intergroup Phase II study SWOG S0432", Leukemia Research, vol. 38, Issue 3, Mar. 2014, p. 329-333, DOI:https://doi.org/10.1016/j.leukres.2013.12.001.

Erhardt, A., et al., "Treatment of chronic hepatitis delta with pegylated interferon-a2b", Liver international: official journal of the International Association for the Study of the Liver, vol. 26, No. 7, Sep. 2006, p. 805-810, DOI: 10.1111/j.1478-3231.2006.01279.x.

Etzion, O., et al., "Noninvasive Tests For Detection Of Biopsy-proven Cirrhosis in Chronic Hepatitis D Infected Patients Are Suboptimal", American Association for the Study of Liver Diseases (AASLD), The Liver Meeting Digital Experience (TLMdX) 2020, hosted Nov. 13-16, 2020, 1 page.

Extended European Search Report dated Apr. 26, 2018 in European Patent Application No. 15865819.5, 8 pages.

Extended European Search Report dated Dec. 7, 2018 in European Patent Application No. 16783855.6, 4 pages.

Extended European Search Report dated Oct. 13, 2017 in European Patent Application No. 15785846.5, 9 pages.

Gastroenterology, Annual Abstract Supplement, vol. 142, Issue 4, Supplement 2, (2007), p. A765.

Ghosal, A., et al., "Identification of Human Liver Cytochrome P450 Enzymes Responsible For The Metabolism of Lonafarnib (Sarasar)", Drug Metabolism and Disposition, vol. 34, No. 4, Jan. 27, 2006, p. 628-635, DOI:10.1124/dmd.105.007906.

Glenn, J.S., et al. "Identification of a prenylation site in delta virus large antigen" Science, vol. 256, Issue 5061, May 29, 1992, p. 1331-1333, DOI: 10.1126/science.1598578.

Glenn, J.S., et al. "Use of a Prenylation Inhibitor as a Novel Antiviral Agent", Journal of Virology, vol. 72, Issue 11, Nov. 1998, p. 9303-9306, Doi:10.1128/JVI.72.11.9303-9306.1998.

Hanrahan, E.O., et al., "A Phase II Study of Lonafarnib (SCH66336) in Patients With Chemo refractory, Advanced Squamous Cell Carcinoma of the Head and Neck", American Journal of Clinical Oncology, vol. 32, No. 3, Jun. 2009, p. 274-279, DOI:10.1097/COC.0b013e318187dd57.

Heidrich, B., et al. "Treatment options for hepatitis delta virus infections", Curr Infect Dis Rep, vol. 15, No. 1, Feb. 2013, p. 31-38, DOI:10.1007/s11908-012-0307-z.

Heller, T. et al. "Long-term therapy of chronic delta hepatitis with peginterferon alfa." Alimentary pharmacology & therapeutics, vol. 40, Issue 1 (2014) p. 93-104. doi:10.1111/apt.12788.

Hepatology, vol. 60, Supplement 1, Special Issue: The 65th Annual Meeting of the Am. Ass'n for the Study of Liver Diseases, Abstracts (Oct. 2014), p. 308A-309A.

Hill, A., et al. "How much ritonavir is needed to boost protease inhibitors? Systematic review of 17 dose-ranging pharmacokinetic trials", AIDS, vol. 23, Issue 17, Nov. 13, 2009, p. 2237-2245, DOI:10.1097/QAD.0b013e328332c3a5.

(56) References Cited

OTHER PUBLICATIONS

"History of Changes for Study: NCT02430194 Lonafarnib With Ritonavir in Hdv (LOWR-2) (Lowr-2)", submitted Apr. 25, 2015, available at clinicaltrials.gov/ct2/history/NCT02511431?V_2=View#StudyPageTop, 7 pages.

"History of Changes for Study: NCT02511431 Treatment of Chronic Delta Hepatitis With Lonafarnib and Ritonavir", submitted Aug. 11, 2015, available at clinicaltrials.gov/ct2/history/NCT02430194?v_1=View#StudyPageTop, 11 pages.

Hu, Q et al., "Highly efficient miniaturized coprecipitation screening (MiCoS) for amorphous solid dispersion formulation development," International Journal of Pharmaceutics, vol. 450, Issues 1-2, Jun. 25, 2013, p. 53-62, DOI:https://doi.org/10.1016/j.ijpharm.2013.04.040.

Hull, M.W. et al., "Ritonavir-boosted protease inhibitors in HIV therapy," Annals of Medicine, vol. 43, Issue 5, 2011, p. 375-388, DOI:10.3109/07853890.2011.572905.

International Preliminary Report on Patentability dated Jun. 6, 2017 in International Patent Application No. PCT/US2015/063674, 9 pages.

International Preliminary Report on Patentability dated May 8, 2018 in International Patent Application No. PCT/US2016/058937, 8 pages.

International Preliminary Report on Patentability dated Nov. 1, 2016 in International Patent Application No. PCT/US2015/028933, 5 pages.

International Preliminary Report on Patentability dated Oct. 24, 2017 in International Patent Application No. PCT/US2016/028651, 7 pages.

International Search Report and Written Opinion dated Feb. 23, 2016 in International Patent Application No. PCT/US2015/063674, 12 pages.

International Search Report and Written Opinion dated Jul. 15, 2015 in International Patent Application No. PCT/US2015/028933, 5 pages.

International Search Report and Written Opinion dated Jul. 26, 2016 in International Patent Application No. PCT/US2016/028651, 15 pages.

International Search Report and Written Opinion dated Mar. 2, 2017 in International Patent Application No. PCT/US2016/058937, 13 pages.

Chiba, H., "Interaction with drug metabolism", Japanese Journal of Clinical Pharmacology and Therapeutics, vol. 31, No. 3, May 2000, pp. n527-528.

Karatayli, E., et al. "A one step real time PCR method for the quantification of hepatitis delta virus RNA using an external armored RNA standard and intrinsic internal control.", Journal of Clinical Virology, vol. 60, Issue 1, May 2014, p. 11-15, DOI:10.1016/j.jcv.2014.01.021.

Kodani, M., et al., "One-step real-time PCR assay for detection and quantitation of hepatitis D virus RNA", Journal of Virological Methods, vol. 193, Issue 2, Nov. 2013, p. 531-535, DOI:10.1016/j.jviromet.2013.07.033.

Koh, C., et al., "Oral prenylation inhibition with lonafarnib in chronic hepatitis D infection: a proof-of-concept randomized, double-blind, placebo-controlled phase 2A trial", Lancet Infect Dis, vol. 15, No. 10, Oct. 2015, p. 1167-1174, Doi: 10.1016/S1473-3099(15)00074-2.

Koh, C., et al., "Prenylation inhibition with lonafarnib decreases hepatitis D levels in humans," Hepatology, ASSLD Abstracts, Abstract No. 1860, vol. 60, No. 4, Oct. 2014, p. 1092A-1093A.

Lau, D.T., et al., "Lamivudine for chronic delta hepatitis", Hepatology, vol. 30, Issue 2, Aug. 1999, p. 546-549, DOI:https://doi.org/10.1002/hep.510300217.

Li, S., et al., "Effect of hepatitis B virus infection on human P450 3 A4", Nal Med J. China, vol. 86, No. 38, Oct. 17, 2006, p. 2703-2706.

Liaw, Y.F., "Hepatitis flares and hepatitis B e antigen seroconversion: Implication in anti-hepatitis B virus therapy" Journal of Gastroenterology and Hepatology, vol. 18, Issue 3, Feb. 26, 2003, p. 246-252, DOI:https://doi.org/10.1046/j.1440-1746.2003.02976.x.

Limdi, J.K., et al. "Evaluation of abnormal liver function tests", Postgraduate Medical Journal, vol. 79, Issue 932, year 2003, p. 307-312, DOI: 10.1136/pmj.79.932.307.

List A.F., et al., "Phase I study of continuous oral administration of lonafarnib (Sarasar) in patients with advanced hematologic malignancies", Blood, vol. 100, year 2002, p. 789a.

Liu, Y.P., et al. "Rapid and quantitative detection of hepatitis B virus", World Journal of Gastroenterology, vol. 21, Issue 42, Nov. 14, 2015, p. 11954-11963, DOI:10.3748/wjg.v21.i42.11954.

Lucia, M.B., et al. "HIV-Protease Inhibitors Contribute to p. Glycoprotein Efflux Function Defect in Peripheral Blood Lymphocytes From HIV-Positive Patients Receiving Haart", JAIDS (Journal of Acquired Immune Deficiency Syndromes), vol. 27, Issue 4, Aug. 1, 2001, p. 321-330.

Mandorfer, M., et al. "Changes in Hepatic Venous Pressure Gradient Predict Hepatic Decompensation in Patients Who Achieved Sustained Virologic Response to Interferon-Free Therapy." Hepatology (Baltimore, Md.) vol. 71, Issue 3 (2020): 1023-1036. doi:10.1002/hep.30885.

Masci, P., et al. "New and modified interferon alfas: Preclinical and clinical data", Current Oncology Reports, vol. 5, Apr. 2003, p. 108-113, DOI:https://doi.org/10.1007/s11912-003-0097-4.

Miller, M.M., et al. "The role of dolutegravir in the management of HIV infections", Infection and Drug Resistance, vol. 8, Feb. 19, 2015, p. 19-29, DOI:https://doi.org/10.2147/IDR.S58706.

Myler, H., et al., "Anti-PEG antibody bioanalysis: a clinical case study with PEG-IFN-λ-1a and PEG-IFN-α2α in naive patients", Bioanalysis, vol. 7, Issue 9 (2015): 1093-1106. DOI:10.4155/bio.15.36.

Ning, L., "Pharmaceutics", Planned Textbook for Pharmacy and Bioengineering in Colleges and Universities, No. 186643, Dec. 31, 2007, p. 273-276.

Noureddin, M., et al., "Hepatitis delta: epidemiology, diagnosis and management 36 years after discovery", Curr Gastroenterol Rep., vol. 16, Issue 365, Jan. 2014, 8 pages, DOI:10.1007/s11894-013-0365-x.

Osborn, B. L., et al. "Pharmacokinetic and Pharmacodynamic Studies of a Human Serum Albumin-Interferon-α Fusion Protein in Cynomolgus Monkeys", The Journal of Pharmacology and Experimental Therapeutics, vol. 303, No. 2, year 2002, p. 540-548, DOI:https://doi.org/10.1124/jpet.102.037002.

Otto, J.C., et al. "The Hepatitis Delta Virus Large Antigen Is Farnesylated Both in Vitro and in Animal Cells", The Journal of Biological Chemistry, vol. 271, No. 9, Mar. 1, 1996, p. 4569-4572, DOI:10.1074/jbc.271.9.4569.

Piyachaturawat, P. et al. "Changes in transient elastography in early cirrhotic patients after receiving nonselective B-blocker for primary variceal bleeding prophylaxis: Three-month follow up." JGH open : an open access journal of gastroenterology and hepatology, vol. 2, Issue 5, p. 172-177. (2018) doi:10.1002/jgh3.12063.

Replacement Supplemental Extended European Search Report dated Nov. 24, 2017 in European Patent Application No. 15785846.5, 8 pages.

Saldanha, J., et al. "An international collaborative study to establish a World Health Organization international standard for hepatitis B virus DNA nucleic acid amplification techniques", Vox Sanguinis, vol. 80, Issue 1, Jan. 2001, p. 63-71, DOI:10.1046/j.1423-0410.2001.00003.x.

Tho, I., et al. "Formation of nano/micro-dispersions with improved dissolution properties upon dispersion of ritonavir melt extrudate in aqueous media", European Journal of Pharmaceutical Sciences, vol. 40, Issue 1, Apr. 2010, p. 25-32, DOI:https://doi.org/10.1016/j.ejps.2010.02.003.

Tong, W., et al. "Identification of unstable metabolites of Lonafarnib using liquid chromatography-quadrupole time-of-flight mass spectrometry, stable isotope incorporation and ion source temperature alteration", Journal of Mass Spectrometry, vol. 41, Issue 11, Nov. 2006, p. 1430-1441, DOI:10.1002/jms.1114.

(56) References Cited

OTHER PUBLICATIONS

Velasco, M., et al. "Resolution of Chronic Hepatitis B after Ritonavir Treatment in an HIV-Infected Patient," The New England Journal of Medicine, vol. 340, No. 22, 1999, p. 1765-1766.

Wang, X., et al. "Derivation of Phase 3 dosing for peginterferon lambda-1a in chronic hepatitis C, Part 1: Modeling optimal treatment duration and sustained virologic response rates", The Journal of Clinical Pharmacology, vol. 55, Issue 1, (2015), p. 63-72, DOI:10.1002/jcph.363.

Wedemeyer, H., et al., "Epidemiology, pathogenesis and management of hepatitis D: update and challenges ahead", Nature Reviews Gastroenterology and Hepatology, vol. 7, Jan. 2010, p. 31-40, DOI:https://doi.org/10.1038/nrgastro.2009.205.

Yang et al., "Different alterations of cytochrome P450 3A4 isoform and its gene expression in livers of patients with chronic liver diseases," World Journal of Gastroenterology 2003;9(2): 359-363; www.wjgent.com.

Yardeni, D., et al., Regression of Liver Fibrosis Following 48 Weeks Of Therapy with Peginterferon Lambda in Patients with Chronic Hepatitis Delta Virus (HDV) Infection, American Association for the Study of Liver Diseases (AASLD), The Liver Meeting Digital Experience (TLMdX) 2020, hosted Nov. 13-16, 2020, 1 page.

Yu, L., et al., "Amorphous pharmaceutical solids: preparation, characterization and stabilization", Advanced Drug Delivery Reviews, vol. 48, 2001, p. 27-42.

Yurdaydin, C., et al., "Optimizing The Prenylation Inhibitor Lonafarnib Using Ritonavir Boosting in Patients with Chronic Delta Hepatitis" Journal of Hepatology, vol. 62, Supplement 2, Apr. 2015, p. S252, DOI:https://doi.org/10.1016/S0168-8278(15)30137-9.

Zhang, F.L., et al. "Protein Prenylation: Molecular Mechanisms and Functional Consequences", Annual Review of Biochemistry, vol. 65, Jul. 1996, p. 241-269, DOI:10.1146/annurev.bi.65.070196.001325.

* cited by examiner

PHARMACEUTICAL COMPOSITIONS COMPRISING LONAFARNIB AND RITONAVIR

CROSS-REFERENCE TO RELATED APPLICATIONS

This is a continuation of U.S. application Ser. No. 17/073,920, filed Oct. 19, 2020, which is a continuation of U.S. application Ser. No. 15/567,444, filed Oct. 18, 2017, which is a national stage application under 35 U.S.C. § 371 of International Application No. PCT/US2016/028651, filed Apr. 21, 2016, which claims priority to U.S. Provisional Application No. 62/150,721, filed Apr. 21, 2015, and to U.S. Provisional Application No. 62/153,815, filed Apr. 28, 2015, the contents of each of which are incorporated by reference herein.

FIELD OF THE INVENTION

Provided are pharmaceutical compositions for providing lonafarnib and ritonavir cotherapy and methods for use of those compositions for treating viral hepatitis resulting from hepatitis delta virus (HDV) infection. Thus, the present invention relates to the fields of biology, chemistry, medicinal chemistry, medicine, molecular biology, and pharmacology.

BACKGROUND OF THE INVENTION

Hepatitis delta virus (HDV) is a virus that causes the most severe form of viral hepatitis, for which currently there is not an effective medical therapy. HDV always presents as a co-infection with hepatitis B virus (HBV), and a co-infected patient is much more likely to die of complications of viral infection than a patient infected with HBV alone.

The HDV large delta antigen protein contains a CXXX box rendering it a substrate for prenylation (see Zhang and Casey, 1996, Annu. Rev. Biochem. 65:241-269) by the prenyl lipid farnesyltransferase (see Glenn et al., 1992, Science 256:1331-1333, and Otto and Casey, 1996, J. Biol. Chem. 271:4569-4572). Farnesylation of proteins catalyzed by FTase is an essential step in processing of a variety of proteins and occurs by transfer of the farnesyl group of farnesyl pyrophosphate to a cysteine at the C-terminal tetrapeptide of a protein in a structural motif sometimes referred to as the CAAX box. Further post-translational modifications of a farnesylated protein, including proteolytic cleavage at the cysteine residue of the CAAX box and methylation of the cysteine carboxyl, generally follow farnesylation. Molecular genetic experiments demonstrated that specific mutation of the prenylation site in large delta antigen prevents both its prenylation and HDV particle formation (see Glenn et al., 1992, supra). PCT Pub. No. WO 2011/088126, incorporated herein by reference, describes the potential of using prenyltransferase inhibitors, including lonafarnib, in humans to treat HDV infection. However, there continues to be an ongoing need for agents to treat HDV infection.

BRIEF SUMMARY OF THE INVENTION

Provided is an amorphous co-precipitate comprising lonafarnib or a pharmaceutically acceptable salt thereof, ritonavir or a pharmaceutically acceptable salt thereof, and a co-polymer.

Also provided is a pharmaceutical composition for use in a method of treating a hepatitis delta virus (HDV) infection in a human or in a method of reducing hepatitis delta virus ribonucleic acid (HDV-RNA) in a human infected with HDV comprising a therapeutically effective amount of an amorphous co-precipitate comprising lonafarnib or a pharmaceutically acceptable salt thereof, ritonavir or a pharmaceutically acceptable salt thereof, and a co-polymer as described herein.

Also provided is a method of treating a hepatitis delta virus (HDV) infection in a human, said method comprising administering to the human in need of such treatment a pharmaceutical composition comprising lonafarnib or a pharmaceutically acceptable salt thereof, ritonavir or a pharmaceutically acceptable salt thereof, and a co-polymer as described herein, thereby treating the HDV infection.

Also provided is a method of reducing hepatitis delta virus ribonucleic acid (HDV-RNA) in a human infected with HDV, said method comprising administering to the human a pharmaceutical composition comprising lonafarnib or a pharmaceutically acceptable salt thereof, ritonavir or a pharmaceutically acceptable salt thereof, and a co-polymer as described herein, whereby the viral load of HDV is reduced by at least 2 log HDV-RNA copies/mL.

Also provided is a process for the preparation of an amorphous co-precipitate comprising lonafarnib or a pharmaceutically acceptable salt thereof, ritonavir or a pharmaceutically acceptable salt thereof, and a co-polymer as described herein.

These and other aspects and embodiments of the invention are described in more detail below.

DETAILED DESCRIPTION OF THE INVENTION

Figure 1A:
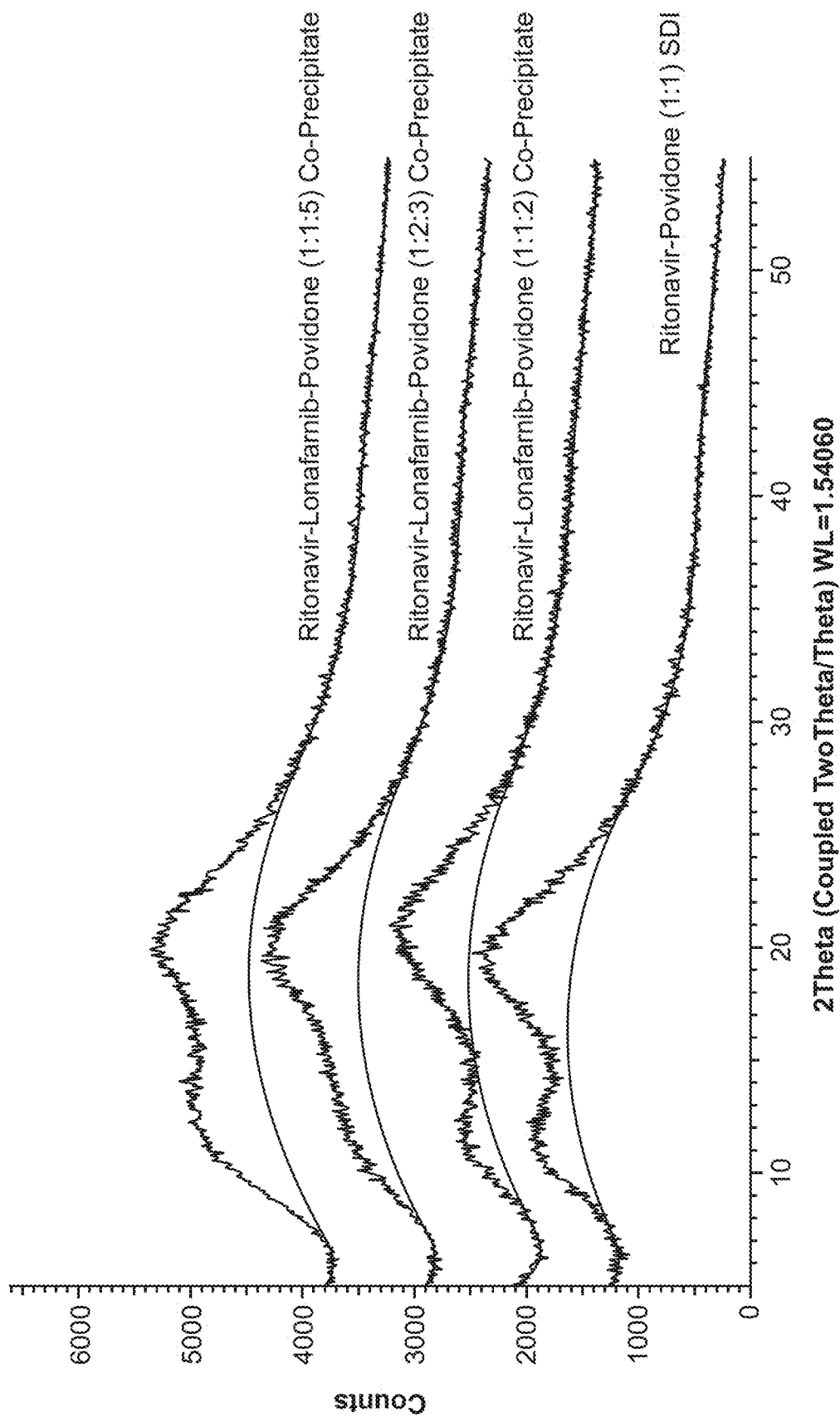
FIG. 1A-B. X-ray diffraction patterns. (A) Characteristic powder X-ray diffraction (XRPD) patterns of amorphous forms of (1:1:2), (1:2:3), and (1:1:5) EBP994 (lonafarnib) and ritonavir co-precipitates prepared as described in Example 1. (B) Characteristic XRPD pattern of crystalline ritonavir used as starting material.
Figure 1B:
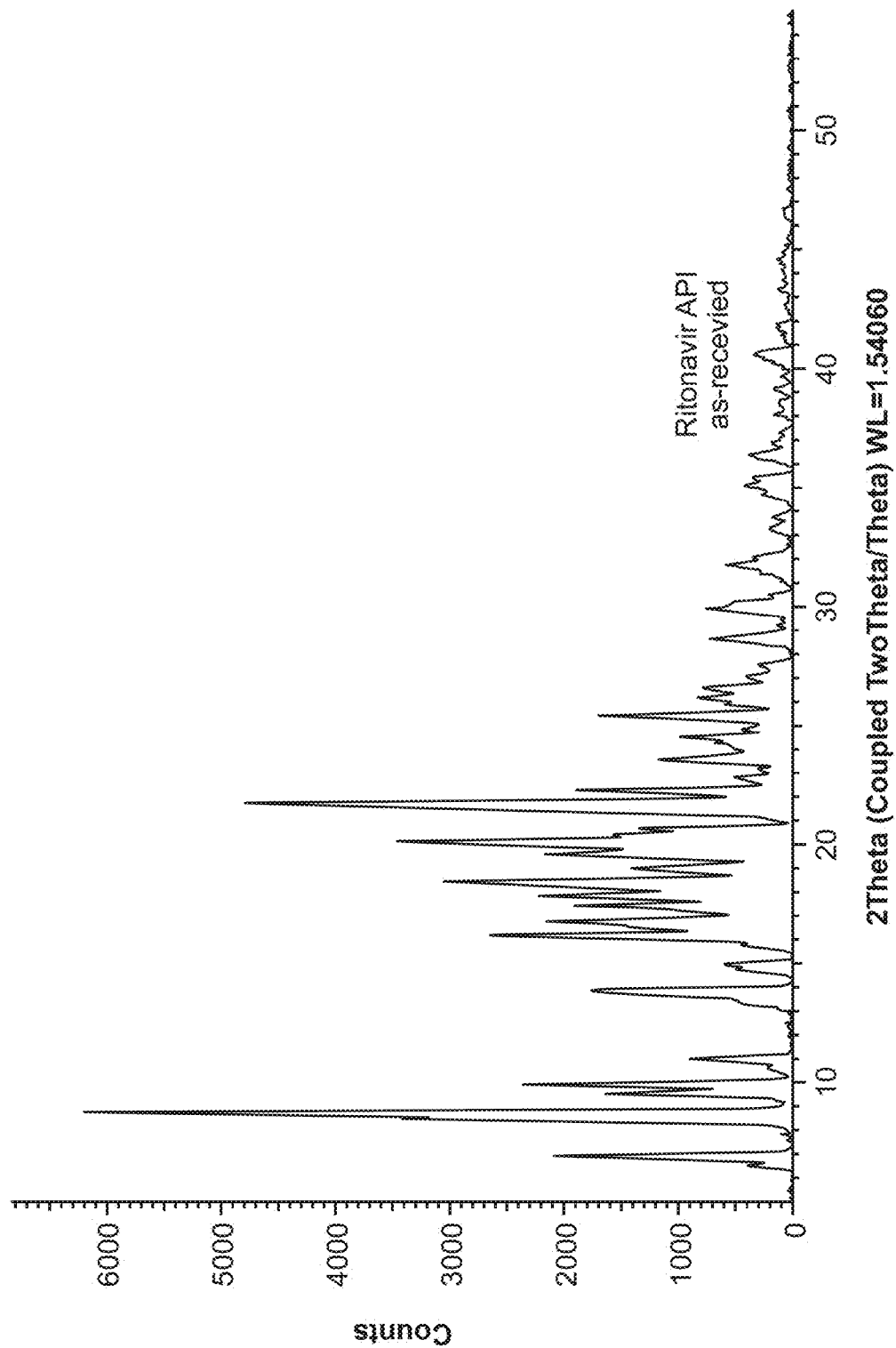

This detailed description of the invention is divided into sections for the convenience of the reader. As will be apparent to those of skill in the art upon reading this disclosure, each of the individual embodiments described and illustrated herein has discrete components and features which may be readily separated from or combined with the features of any of the other several embodiments (whether described in the same or different sections of this disclosure) without departing from the scope or spirit of the present disclosure. Any recited method can be carried out in the order of events recited or in any other order that is logically possible. Embodiments of the present disclosure will employ, unless otherwise indicated, techniques of synthetic organic chemistry, biochemistry, biology, molecular biology, recombinant DNA techniques, pharmacology, and the like, within the skill of the art and explained in the relevant scientific literature. This disclosure is not limited to particular embodiments described, and the embodiment of the invention in practice may, of course, vary from that described herein.

I. Introduction

In one aspect, the present invention relates to compositions for the treatment of HDV infection. The present invention arises in part out of the discovery of how to co-formulate lonafarnib and ritonavir to provide suitable unit dosage forms for patients in need of such combination therapies. As described in the Examples section below, in clinical trials with patients infected with HDV, lonafarnib-ritonavir co-therapy using separately formulated drugs reduced HDV viral load substantially, including, in one case, to undetectable levels. See, Example 3 and FIG. 5. The present invention makes possible the treatment of HDV-infected patients with unit dosage forms conveniently comprising both drugs formulated for oral administration. Thus, in one aspect, compositions comprising lonafarnib and ritonavir are provided herein. In some embodiments, the compositions comprise an amorphous co-precipitate of lonafarnib, ritonavir, and a copolymer.

In another aspect, therapeutic methods for the treatment of HDV infection are provided, wherein the method comprises administering a lonafarnib and ritonavir pharmaceutical composition comprising an amorphous co-precipitate of lonafarnib, ritonavir, and a copolymer as described herein. In some embodiments, lonafarnib and ritonavir each are administered orally on a continuous, daily basis, at least once per day (QD), and in various embodiments two times per day (BID) as a pharmaceutical composition comprising an amorphous co-precipitate of lonafarnib, ritonavir, and a copolymer as described herein.

II. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about".

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

The term "lonafarnib," also referred to herein as "EBP994", and also known under the trade name Sarasar® (Schering), refers to a farnesyltransferase (FTase) inhibitor, 4(2[4-[(11R)-3,10-dibromo-8-chloro-6,11-dihydro-5Hbenzo[5,6]-cyclohepta[1,2b]pyridin-11yl]-piperidino]-2-oxoethyl]-1-piperidinecarboxamide), which has the structure shown below:

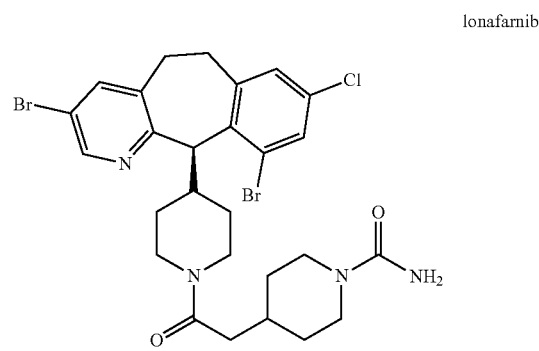 [SMILES: NC(=O)N1CCC(CC(=O)N2CCC([C@H]3c4ncc(Br)cc4CCc4cc(Cl)cc(Br)c43)CC2)CC1]

lonafarnib

Lonafarnib is a solid with a melting point of approximately 200° C. and is non-hygroscopic. Its molecular weight is 638.7. In the solid state, the compound is thermally stable. In solution, it is stable at neutral pH but will hydrolyze in acidic or basic conditions. It is a poorly water soluble tricyclic compound, which when formulated in crystalline forms results in low and variable bioavailability in animals. In pharmaceutical dosage forms, lonafarnib may be administered in the form of its pharmaceutically acceptable salts, or pharmaceutically acceptable solvates of lonafarnib and its salts, or may be used alone or in appropriate association, as well as in combination, with other pharmaceutically active compounds.

The term "ritonavir" refers to a protease inhibitor and Cytochrome P450 CYP3A inhibitor, (5S,8S,10S,11S)-10-Hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid 5-thiazolylmethyl ester, also known under the trade name Norvir® (Abbott Laboratories). Ritonavir and processes for preparing ritonavir as disclosed in U.S. Pat. Nos. 5,648,497 and 5,541,206, each of which is incorporated by reference herein.

Ritonavir is known to exist in different polymorphic forms, which may differ from each other in terms of stability, physical properties, spectral data, and methods of preparation. In some embodiments, ritonavir is in an amorphous form. Amorphous ritonavir and methods of preparing amorphous ritonavir are described in the art. See, e.g., U.S. Pat. Nos. 7,148,459, 7,183,416, and 9,096,556, each of which is incorporated by reference herein.

The term "amorphous," as used herein, refers to a solid in which the particles which comprise the solid are not arranged in a regular or predictable pattern. In some embodiments, an amorphous solid is characterized by poorly defined patterns when exposed to X-rays.

The term "essentially free of crystalline forms of ritonavir," as used with reference to a composition, means that no crystalline polymorph forms of ritonavir are detectable in the composition, for example, as detected by a powder X-ray diffractometer.

As used herein, the term "polymer" refers to an organic substance composed of a plurality of repeating structural units (monomeric units) covalently linked to one another. The term "polymer" as used herein encompasses organic and inorganic polymers. The term "copolymer" or "co-polymer" as used herein refers to a polymer that comprises two or more different monomeric units. A co-polymer may comprise any arrangement of the two or more different monomeric units, including but not limited to alternating co-polymers, periodic co-polymers, random co-polymers, block co-polymers, and branched co-polymers.

The term "coprecipitate" or "co-precipitate," as used with reference to a lonafarnib-ritonavir-copolymer co-precipitate, refers to a composition prepared by removing solvent from a solution comprising lonafarnib or pharmaceutically acceptable salt thereof, ritonavir or pharmaceutically acceptable salt thereof, and a co-polymer.

The term "amorphous co-precipitate substantially free of crystalline forms of ritonavir," as used with reference to a co-precipitate comprising lonafarnib and ritonavir as described herein, refers to an amorphous form of a co-precipitate of lonafarnib and ritonavir that contains less than about 5 percent (w/w) crystalline forms of ritonavir. In some embodiments, an amorphous co-precipitate that is substantially free of crystalline forms of ritonavir contains less than 1 percent (w/w) crystalline forms of ritonavir. In some embodiments, an amorphous co-precipitate that is substantially free of crystalline forms of ritonavir is essentially free of crystalline forms of ritonavir.

The term "pharmaceutical composition," as used herein, refers to a composition suitable for administration to a human and/or animal subject. In some embodiments, a "pharmaceutical composition" is sterile and/or free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intratracheal, intramuscular, subcutaneous, inhalational and the like.

As used herein, a "pharmaceutically acceptable" component (e.g., pharmaceutically acceptable excipient, pharmaceutically acceptable diluent, pharmaceutically acceptable carrier, or pharmaceutically acceptable salt) is one that is suitable for use with humans and/or animals without undue adverse side effects (such as toxicity, irritation, or allergic response) commensurate with a reasonable benefit/risk ratio.

The term "salt(s)", as used herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

The terms "patient", "host," or "subject," as used interchangeably herein, refer to a human infected with HDV.

The term "HDV infection," as used herein with respect to a human (host) refers to a host having a hepatitis delta virus (HDV) infection. In some embodiments, the host having an HDV infection is characterized for the level of virus that is present in the host, e.g., by measuring the number of HDV RNA copies. In some embodiments, a sample (e.g., a blood, fluid, cell, or tissue sample, e.g., a serum or plasma sample) is obtained from a host having an HDV infection for measuring the level of virus that is present in the sample (e.g., for measuring the number of HDV RNA copies). In some embodiments, an HDV infected human host has a viral load of HDV-RNA of at least about 2 log HDV-RNA copies/mL of host serum or plasma or $10^2$ copies of HDV-RNA/mL of host serum or plasma, e.g., at least about 3 log HDV-RNA copies/mL of host serum or plasma or $10^3$ copies of HDV-RNA/mL of host serum or plasma, or at least about 4 log HDV-RNA copies/mL of host serum or plasma or $10^4$ copies of HDV-RNA/mL of host serum or plasma, such as about 4 log HDV-RNA copies/mL of host serum or plasma to 7 log HDV-RNA copies/mL of host serum or plasma or $10^4$-$10^7$ copies of HDV-RNA/mL of host serum or plasma.

The term "HDV-RNA viral load" or "viral load," as used with reference to a sample such as a human serum or plasma sample, refers to the number of copies of human HDV-RNA in a given amount of human serum or plasma sample. HDV-RNA viral load can be measured according to methods known in the art. Currently, there is one commercially available test for the detection of HDV-RNA (Quest Therapeutics), but no commercially available clinical tests for the quantitation of HDV-RNA in clinical samples. However, several assays for quantitation of HDV-RNA reported in the literature (e.g., Kodani et al. 2013 J. Virol. Methods, 193(2), 531; and Karatayli et al, 2014, J. Clin. Virol, 60(1), 11) utilize a quantitative real-time reverse transcription-polymerase chain reaction (qRT-PCR) assay for quantification of HDV-RNA in serum or plasma suitable for use in accordance with the methods described herein. The amount of signal generated during the assay is proportional to the amount of HDV-RNA in the sample. The signal from the test sample is compared to that of a dilution series of a quantified Hepatitis Delta RNA standard, and a copy number of genome copies is calculated.

The terms "administer," "administering," and "administration" refer to introducing a compound, a composition, or an agent (e.g., an amorphous co-precipitate as described herein or a pharmaceutical composition comprising an amorphous co-precipitate as described herein) into a host, such as a human. As used herein, the terms encompass both direct administration, which may be administration to a patient by a medical professional or may be self-administration, and indirect administration, such as the act of prescribing a compound, composition, or agent.

As used herein, administering "separately formulated lonafarnib and ritonavir" refers to treating a patient by administering lonafarnib and ritonavir as separate unit dosage forms (i.e., not coformulated).

The term "therapeutically effective amount" as used herein refers to that amount of an embodiment of the agent (which may be referred to as a compound, an inhibitory agent, and/or a drug) being administered that will treat to some extent a disease, disorder, or condition, e.g., relieve one or more of the symptoms of the disease, i.e., infection, being treated, and/or that amount that will prevent, to some extent, one or more of the symptoms of the disease, i.e., infection, that the subject being treated has or is at risk of developing.

The terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a human subject, and includes: (a) reducing the risk of occurrence of the disease in a subject determined to be predisposed to the disease but not yet diagnosed as infected with the disease, (b) impeding the development of the disease, and/or (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen viral load, reduction of disease symptoms, etc.).

The term "unit dosage form," as used herein, refers to physically discrete units suitable as unitary dosages for human subjects, each unit containing a predetermined quantity of a compound (e.g., lonafarnib and/or ritonavir as described herein) or compounds, calculated in an amount sufficient to produce the desired treatment effect in association with a pharmaceutically acceptable diluent, carrier or vehicle.

The term "oral dosage form," as used herein, refers to a unit dosage form that is orally administered.

The term "release" includes the provision (or presentation) of drug from a formulation to body tissues and/or fluids, such as those within the gastrointestinal tract. Generally, release refers to the release of significant amounts of drug. For instance, although in some instances a small portion of the drug may be released prematurely, this is generally less than 10% wt. (typically less than 5% or less than 1%) of the total drug in the formulation. In an embodiment, release is gauged by monitoring the concentration of drug in blood, serum or plasma. In another embodiment, release is monitored through the therapeutic effect produced by the drug. Alternatively, release can be gauged from an in vitro model such as an in vitro dissolution profile in an appropriate bio-relevant media such as phosphate buffer or simulated gastric fluid. It is understood that the exact time of release can vary within a unit dosage form. Thus, when release is stated herein to occur at a specified time, then it can be understood that the time specified is an average time of release.

All percentages are % w/w, unless specifically indicated otherwise. It will be appreciated that due to rounding or practical limits on quantitative measurements, reference to a quantity of API or excipient in a dosage form can include some variation, such as ±0.10% or ±0.5%.

III. Amorphous Co-Precipitates Comprising Lonafarnib and Ritonavir and Methods of Making Co-Precipitates In one aspect, amorphous co-precipitates comprising lonafarnib or a pharmaceutically acceptable salt thereof, ritonavir or a pharmaceutically acceptable salt thereof, and a co-polymer are provided. In another aspect, pharmaceutical compositions comprising amorphous co-precipitates comprising lonafarnib or a pharmaceutically acceptable salt thereof, ritonavir or a pharmaceutically acceptable salt thereof, and a co-polymer are provided.

In some embodiments, an amorphous co-precipitate comprising lonafarnib or a pharmaceutically acceptable salt thereof, ritonavir or a pharmaceutically acceptable salt thereof, and a co-polymer is prepared by dissolving the lonafarnib or pharmaceutically acceptable salt thereof, the ritonavir or pharmaceutically acceptable salt thereof, and the co-polymer in a solvent to form a solution, and then substantially removing the solvent from the solution to yield an amorphous co-precipitate. Methods for the preparation of amorphous co-precipitates are described in further detail below.

Preparation of Amorphous Co-Precipitates

The amorphous co-precipitates of the present invention are prepared using lonafarnib or a pharmaceutically acceptable salt thereof and ritonavir or a pharmaceutically acceptable salt thereof. The term "pharmaceutically acceptable salt," as used herein, refers to those salts that retain the biological effectiveness and optionally other properties of the free bases and that are obtained by reaction with inorganic or organic acids, such as but not limited to hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Reference to an agent herein (e.g., lonafarnib or ritonavir) is understood to include reference to salts thereof, unless otherwise indicated. If a salt or a solvate is used, equivalently larger amounts will be required as is readily understood by the skilled artisan.

Unless otherwise indicated, the starting material for making co-precipitates as described herein include crystalline and amorphous forms of lonafarnib and ritonavir or their pharmaceutically acceptable salts, including, for example, solvated polymorphs (including hydrates), unsolvated polymorphs (including anhydrates), pseudopolymorphs, conformational polymorphs of the compounds, as well as mixtures thereof.

All deuterated analogs (a compound is a deuterated analog of another compound, the "parent compound", if it differs from the parent compound by only replacement of one or more hydrogen atoms with one or more deuterium atoms) of any active pharmaceutical ingredient described herein, including without limitation, lonafarnib and ritonavir, are, for purposes of the present invention, encompassed by reference to the parent compound.

All stereoisomers of any agent described herein, including without limitation, lonafarnib, ritonavir, and any other active pharmaceutical agent described herein, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

In some embodiments, the co-polymer is chosen from polyvinylpyrrolidone, hydroxypropyl cellulose, hydroxypropyl methylcellulose (HPMC), hypromellose phthalate, polyvinylpyrrolidone-vinylacetate copolymer, hypromellose-acetate-succinate, and mixtures thereof.

In some embodiments, the co-polymer is polyvinylpyrrolidone (also known as povidone or PVP). In some embodiments, the co-polymer is polyvinylpyrrolidone K12 (povidone K12), polyvinylpyrrolidone K17 (povidone K17), polyvinylpyrrolidone K25 (povidone K25), polyvinylpyrrolidone K30 (povidone K30), or polyvinylpyrrolidone K90 (povidone K90). In some embodiments, the polyvinylpyrrolidone is polyvinylpyrrolidone K30.

In some embodiments, the co-polymer is polyvinylpyrrolidone-vinylacetate copolymer. In some embodiments, the polyvinylpyrrolidone-vinylacetate copolymer is a copolymer of 1-vinyl-2-pyrrolidone and vinyl acetate in a ratio of 6:4 by mass. In some embodiments, the polyvinylpyrrolidone-vinylacetate copolymer is Kollidon® VA 64 copovidone.

In some embodiments, the co-polymer is hydroxypropyl methylcellulose (HPMC).

In some embodiments, the solvent is a suitable organic solvent. In some embodiments, the solvent is chosen from dichloromethane, chloroform, isopropyl alcohol, methanol, ethanol, acetone, ethyl methyl ketone, methyl isobutyl ketone, DMSO, water, and mixtures thereof. In some embodiments, the solvent is chosen from dichloromethane, water, and mixtures thereof.

In some embodiments, the process for the preparation of an amorphous co-precipitate comprises: providing a spray solution of the lonafarnib or a pharmaceutically acceptable salt thereof, the ritonavir or a pharmaceutically acceptable salt thereof, and the co-polymer in a solvent; optionally filtering the spray solution to remove insoluble matter; and substantially removing the solvent from the spray solution to yield the amorphous co-precipitate.

As used herein, the term "spray solution" refers to a solution comprising the lonafarnib or pharmaceutically acceptable salt thereof, ritonavir or pharmaceutically acceptable salt thereof, and co-polymer dispersed in the solvent.

In some embodiments, the amount of total solids in the spray solution is less than 10%. In some embodiments, the amount of total solids in the spray solution is less than 5%. In some embodiments, the amount of total solids in the spray solution is about 3%.

In some embodiments, removal of the solvent is accomplished by distillation or complete evaporation of the solvent, spray drying, vacuum drying, tray drying, lyophilization or freeze drying, agitated thin-film drying, or a combination thereof.

In some embodiments, removal of the solvent is accomplished by spray drying. The term "spray drying" broadly refers to processes involving breaking up liquid mixtures into small droplets (atomization) and rapidly removing solvent from the mixture. In a typical spray drying apparatus, a strong driving force evaporates the solvent from the droplets, which may be provided by providing a drying gas. Spray drying processes and equipment are described in Perry's Chemical Engineer's Handbook, pp. 20-54 to 20-57 (Sixth Edition 1984). By way of non-limiting example only, the typical spray drying apparatus comprises a drying chamber, atomizing means for atomizing a solvent-containing feed into the drying chamber, a source of drying gas that flows into the drying chamber to remove solvent from the atomized-solvent-containing feed, an outlet for the products of drying, and product collection means located downstream from the drying chamber. Typically, the product collection means includes a cyclone connected to the drying apparatus. In the cyclone, the particles produced during spray drying are separated from the drying gas and evaporated solvent, allowing the particles to be collected. A filter may also be used to separate and collect the particles produced by spray drying. In some embodiments, the air inlet temperature to the spray drier used may range from about 50° C. to about 125° C., such as from about 55° C. to about 100° C., for example, from about 50° C. to about 70° C., such as about 60° C., and the outlet air temperature used may range from about 30° C. to about 70° C., such as from about 35° C. to about 65° C., such as about no more than 45° C.

Spray drying may be performed in a conventional manner in the processes described herein. The drying gas may be any suitable gas, although inert gases such as nitrogen, nitrogen-enriched air; and argon are preferred. In some embodiments, nitrogen gas is used. The amorphous co-precipitate produced by spray drying may be recovered by techniques commonly used in the art, such as using a cyclone or a filter.

Removal of solvent may also be accomplished, for example, by substantially complete evaporation of the solvent, concentrating the solution, or distillation of solvent, under inert atmosphere to obtain amorphous co-precipitate.

The amorphous co-precipitate may optionally be further dried in, for example, a Vacuum Tray Dryer, a Rotocon Vacuum Dryer, a Vacuum Paddle Dryer, (non vacuum) Tray drying, fluid bed drying or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 25° C. to about 90° C. The drying can be carried out for any desired time period that achieves the desired result, such as times about 1 to 20 hours. Drying may also be carried out for shorter or longer periods of time depending on the product specifications. Temperatures and pressures will be chosen based on the volatility of the solvent being used and the foregoing conditions should be considered as only a general guidance. Drying can be suitably carried out in a tray dryer, vacuum oven, air oven, or using a fluidized bed drier, spin flash dryer, flash dryer, and the like. Drying equipment selection is well within the ordinary skill in the art.

In some embodiments, the step of substantially removing the solvent comprises removing at least 50%, at least 60%, at least 70%, at least 80%, at least 90%, at least 91%, at least 92%, at least 93%, at least 94%, at least 95%, at least 96%, at least 97%, at least 98%, or at least 99% of the solvent from the resulting co-precipitate that is formed.

In some embodiments, an amorphous co-precipitate as described herein is prepared according to a process described in US Patent Publication Nos. 2010/0029667, 2013/0165371, 2013/0193598, 2014/0017314, 2014/0210117, 2015/0028503, 2015/0273354, or 2015/0374827, incorporated by reference herein.

Characteristics of Amorphous Co-Precipitates

In some embodiments, the amorphous co-precipitate that is formed comprises lonafarnib, or a pharmaceutically acceptable salt thereof, in a therapeutically effective amount. In some embodiments, the amorphous co-precipitate comprises the lonafarnib or pharmaceutically acceptable salt thereof in an amount from about 20 mg to about 100 mg, e.g., from about 25 mg to about 100 mg, or from about 25 mg to about 100 mg. In some embodiments, the amorphous co-precipitate comprises the lonafarnib or pharmaceutically acceptable salt thereof in an amount of about 20 mg, about 25 mg, about 30 mg, about 35 mg, about 40 mg, about 45 mg, about 50 mg, about 60 mg, about 70 mg, about 75 mg, about 80 mg, about 90 mg, or about 100 mg.

In some embodiments, the amorphous co-precipitate comprises ritonavir, or a pharmaceutically acceptable salt thereof, in a therapeutically effective amount. In some embodiments, the amorphous co-precipitate comprises the ritonavir or pharmaceutically acceptable salt thereof in an amount from about 50 mg to about 100 mg, e.g., from about 50 mg to about 75 mg, or from about 75 mg to about 100 mg. In some embodiments, the amorphous co-precipitate comprises the ritonavir or pharmaceutically acceptable salt thereof in an amount of about 50 mg, about 60 mg, about 70 mg, about 75 mg, about 80 mg, about 90 mg, or about 100 mg.

In some embodiments, the amorphous co-precipitate comprises lonafarnib or a pharmaceutically acceptable salt thereof in an amount from about 20 mg to about 100 mg, e.g., from about 25 mg to about 100 mg, or from about 50 mg to about 100 mg, and comprises ritonavir or a pharmaceutically acceptable salt thereof in an amount from about 50 mg to about 100 mg. In some embodiments, the amorphous co-precipitate comprises lonafarnib or a pharmaceutically acceptable salt thereof in an amount of about 25 mg, about 50 mg, about 75 mg, or about 100 mg, and comprises ritonavir or a pharmaceutically acceptable salt thereof in an amount of about 50 mg, about 75 mg, or about 100 mg. In some embodiments, the amorphous co-precipitate comprises lonafarnib or a pharmaceutically acceptable salt thereof in an amount of about 25 mg and comprises ritonavir or a pharmaceutically acceptable salt thereof in an amount of about 100 mg. In some embodiments, the amorphous co-precipitate comprises lonafarnib or a pharmaceutically acceptable salt thereof in an amount of about 50 mg and comprises ritonavir or a pharmaceutically acceptable salt thereof in an amount of about 100 mg. In some embodiments, the amorphous co-precipitate comprises lonafarnib or a pharmaceutically acceptable salt thereof in an amount of about 75 mg and comprises ritonavir or a pharmaceutically acceptable salt thereof in an amount of about 100 mg. In some embodiments, the amorphous co-precipitate comprises lonafarnib or a pharmaceutically acceptable salt thereof in an amount of about 100 mg and comprises ritonavir or a pharmaceutically acceptable salt thereof in an amount of about 100 mg.

In some embodiments, the lonafarnib or a pharmaceutically acceptable salt thereof and the ritonavir or a pharmaceutically acceptable salt thereof are present in a ratio of at least 0.5:1 w/w.

In some embodiments, the lonafarnib or a pharmaceutically acceptable salt thereof and the ritonavir or a pharmaceutically acceptable salt thereof are present in a ratio of from 0.5:1 to 2:1 w/w.

In some embodiments, the lonafarnib or a pharmaceutically acceptable salt thereof and the ritonavir or a pharmaceutically acceptable salt thereof are present in a ratio of 0.5:1 w/w.

In some embodiments, the lonafarnib or a pharmaceutically acceptable salt thereof and the ritonavir or a pharmaceutically acceptable salt thereof are present in a ratio of 0.67:1 w/w.

In some embodiments, the lonafarnib or a pharmaceutically acceptable salt thereof and the ritonavir or a pharmaceutically acceptable salt thereof are present in a ratio of 0.75:1 w/w.

In some embodiments, the lonafarnib or a pharmaceutically acceptable salt thereof and the ritonavir or a pharmaceutically acceptable salt thereof are present in a ratio of 1:1 w/w.

In some embodiments, the lonafarnib or a pharmaceutically acceptable salt thereof and the ritonavir or a pharmaceutically acceptable salt thereof are present in a ratio of 1:33 w/w.

In some embodiments, the lonafarnib or a pharmaceutically acceptable salt thereof and the ritonavir or a pharmaceutically acceptable salt thereof are present in a ratio of 1.5:1 w/w.

In some embodiments, the lonafarnib or a pharmaceutically acceptable salt thereof and the ritonavir or a pharmaceutically acceptable salt thereof are present in a ratio of 2:1 w/w.

In some embodiments, the lonafarnib or a pharmaceutically acceptable salt thereof, the ritonavir or a pharmaceutically acceptable salt thereof, and the co-polymer are present in a ratio of 0.5:1:1 w/w.

In some embodiments, the lonafarnib or a pharmaceutically acceptable salt thereof, the ritonavir or a pharmaceutically acceptable salt thereof, and the co-polymer are present in a ratio of 0.5:1:2 w/w.

In some embodiments, the lonafarnib or a pharmaceutically acceptable salt thereof, the ritonavir or a pharmaceutically acceptable salt thereof, and the co-polymer are present in a ratio of 0.66:1:1 w/w.

In some embodiments, the lonafarnib or a pharmaceutically acceptable salt thereof, the ritonavir or a pharmaceutically acceptable salt thereof, and the co-polymer are present in a ratio of 0.66:1:2 w/w.

In some embodiments, the lonafarnib or a pharmaceutically acceptable salt thereof, the ritonavir or a pharmaceutically acceptable salt thereof, and the co-polymer are present in a ratio of 0.75:1:1 w/w.

In some embodiments, the lonafarnib or a pharmaceutically acceptable salt thereof, the ritonavir or a pharmaceutically acceptable salt thereof, and the co-polymer are present in a ratio of 0.75:1:2 w/w.

In some embodiments, the lonafarnib or a pharmaceutically acceptable salt thereof, the ritonavir or a pharmaceutically acceptable salt thereof, and the co-polymer are present in a ratio of 1:1:2 w/w, 1:2:3 w/w, or 1:1:5 w/w.

In some embodiments, the lonafarnib or a pharmaceutically acceptable salt thereof, the ritonavir or a pharmaceutically acceptable salt thereof, and the co-polymer are present in a ratio of 1:1:1 w/w.

In some embodiments, the lonafarnib or a pharmaceutically acceptable salt thereof, the ritonavir or a pharmaceutically acceptable salt thereof, and the co-polymer are present in a ratio of 1:1:2 w/w.

In some embodiments, the lonafarnib or a pharmaceutically acceptable salt thereof, the ritonavir or a pharmaceutically acceptable salt thereof, and the co-polymer are present in a ratio of 1.33:1:1 w/w.

In some embodiments, the lonafarnib or a pharmaceutically acceptable salt thereof, the ritonavir or a pharmaceutically acceptable salt thereof, and the co-polymer are present in a ratio of 1.33:1:2 w/w.

In some embodiments, the lonafarnib or a pharmaceutically acceptable salt thereof, the ritonavir or a pharmaceutically acceptable salt thereof, and the co-polymer are present in a ratio of 1.5:1:1 w/w.

In some embodiments, the lonafarnib or a pharmaceutically acceptable salt thereof, the ritonavir or a pharmaceutically acceptable salt thereof, and the co-polymer are present in a ratio of 1.5:1:2 w/w.

In some embodiments, the lonafarnib or a pharmaceutically acceptable salt thereof, the ritonavir or a pharmaceutically acceptable salt thereof, and the co-polymer are present in a ratio of 2:1:1 w/w.

In some embodiments, the lonafarnib or a pharmaceutically acceptable salt thereof, the ritonavir or a pharmaceutically acceptable salt thereof, and the co-polymer are present in a ratio of 2:1:2 w/w.

In some embodiments, the lonafarnib or a pharmaceutically acceptable salt thereof, the ritonavir or a pharmaceutically acceptable salt thereof, and the co-polymer are present in a ratio of 1:2:3 w/w.

In some embodiments, the lonafarnib or a pharmaceutically acceptable salt thereof, the ritonavir or a pharmaceutically acceptable salt thereof, and the co-polymer are present in a ratio of 1:1:3 w/w.

In some embodiments, the lonafarnib or a pharmaceutically acceptable salt thereof, the ritonavir or a pharmaceutically acceptable salt thereof, and the co-polymer are present in a ratio of 1:1:4 w/w.

In some embodiments, the lonafarnib or a pharmaceutically acceptable salt thereof, the ritonavir or a pharmaceutically acceptable salt thereof, and the co-polymer are present in a ratio of 1:1:5 w/w.

In some embodiments, the amount of drug loading (i.e., the amount of lonafarnib and ritonavir, or pharmaceutically acceptable salts thereof) in the co-precipitate is at least 20%, such as at least 25%, such as at least 30%, such as at least 35%, such as at least 40%, such as at least 45%, such as at least 50%, such as at least 55%, such as at least 60%, such as at least 65%, such as at least 70%.

In some embodiments, the amount of drug loading in the co-precipitate is between 25% and 75%, such as between 25% and 65%, such as between 30 and 50%. In some embodiments, the amount of drug loading in the co-precipitate is about 30%. In some embodiments, the amount of drug loading in the co-precipitate is about 50%.

In some embodiments, the amorphous co-precipitate further comprises a residual amount of solvent. In some embodiments, the solvent is present in the co-precipitate in an amount less than 10%. In some embodiments, the solvent is present in the co-precipitate in an amount less than 5%.

In some embodiments, the co-precipitate is an amorphous co-precipitate that is substantially free of crystalline forms (e.g., contains less than about 5% of crystalline forms of ritonavir and/or lonafarnib, e.g., less than about 4%, less than about 3%, less than about 2%, or less than about 1%). In some embodiments, the co-precipitate is an amorphous co-precipitate is essentially free of crystalline forms.

The amorphous co-precipitate may be characterized by analytical methods known in the art. In some embodiments, X-ray diffraction (XRD) is used to characterize the co-precipitate. In some embodiments, an amorphous co-precipitate is characterized by a powder XRD pattern, showing no well-defined peaks. In some embodiments, the amorphous co-precipitate is characterized by a powder XRD pattern that is substantially in accordance with a powder XRD pattern shown in FIG. 1A.

In some embodiments, the amorphous co-precipitate is stable. The term "stable" refers to stability of the amorphous form under the standard temperature and humidity conditions of testing of pharmaceutical products, wherein the stability is indicated by preservation of the original solid state form. In some embodiments, the term "stable" relates to preservation of the original solid state form after storage for up to 2 weeks, more suitably up to 4 weeks, still more suitably up to 12 weeks, or at least 12 weeks and especially up to 6 months, particularly at least 6 months at 25° C. and 60% relative humidity, 40° C. and 75% relative humidity or at 50° C. and ambient humidity, when protected from moisture is: at least 95% chemically identical to the starting sample and retains an amorphous form.

In some embodiments, each of the lonafarnib and ritonavir, or pharmaceutically acceptable salts thereof, will be at least 96% and, in some embodiments, at least 97% chemically identical to the starting sample after storage for up to 12 weeks, more suitably at least 12 weeks, protected from moisture at 25° C. and 60% relative humidity, 40° C. and 75% relative humidity or at 50° C. and ambient humidity. In some embodiments, the amorphous co-precipitate retains an amorphous form after storage for up to 12 weeks, more suitably at least 12 weeks, protected from moisture at 25° C. and 60% relative humidity, 40° C. and 75% relative humidity or at 50° C. and ambient humidity.

In some embodiments, each of the lonafarnib and ritonavir, or pharmaceutically acceptable salts thereof, may be at least 95%, at least 96%, at least 97% or even at least 98% chemically identical to the starting sample and/or the amorphous co-precipitate retains an amorphous form after storage for up to 6 months, especially at least 6 months, at 25° C. and 60% relative humidity or at 40° C. and 75% relative humidity when protected from moisture. In some cases, each of the lonafarnib and ritonavir, or pharmaceutically acceptable salts thereof, may be at least 99% chemically identical to the starting sample and/or the amorphous co-precipitate retains an amorphous form after storage for up to 6 months, especially at least 6 months, at 25° C. and 60% relative humidity when protected from moisture. Chemical identity to the starting material may be determined using high performance liquid chromatography (HPLC).

IV. Unit Dosage Forms

In another aspect, unit dosage forms comprising an amorphous co-precipitate as described herein are provided. Also provided are pharmaceutical compositions comprising an amorphous co-precipitate as described herein. In some embodiments, the unit dosage forms and pharmaceutical compositions find use in a method of treating a hepatitis delta virus (HDV) infection in a human or in a method of reducing hepatitis delta virus ribonucleic acid (HDV-RNA) in a human infected with HDV.

In some embodiments, the API content of the unit dosage forms is selected so that QD or BID administration delivers a therapeutically effective dose of lonafarnib and ritonavir. In some embodiments, the unit dosage form comprises lonafarnib and ritonavir in the amounts and ratios described in Section III above.

In some embodiments, the unit dosage form is a solid formulation, e.g., a tablet, caplet, gelcap, or other form. In some embodiments, the unit dosage form is a tablet. In some embodiments, the unit dosage form is a capsule.

In some embodiments, the unit dosage form comprises an amorphous co-precipitate as described herein formulated with one or more pharmaceutically acceptable auxiliary substances. In particular, the co-precipitate can be formulated with one or more pharmaceutically acceptable excipients, diluents, carriers, and/or adjuvants.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

In one embodiment, the pharmaceutical formulation is formulated for oral administration. For oral preparations, the co-precipitate can be used alone or in pharmaceutical formulations of the invention comprising, or consisting essentially of, or consisting of the co-precipitate in combination with appropriate additives to make tablets, powders, granules or capsules, for example, with additives, such as lactose, cellulose, calcium phosphates, calcium carbonate, mannitol, sucrose, corn starch or potato starch; with binders, such as crystalline cellulose, cellulose derivatives, acacia, corn starch, lactose, mannitol, or gelatins; with disintegrators, such as corn starch, potato starch or sodium carboxymethylcellulose, sodium starch glycolate, sodium croscarmellose, crospovidone; with lubricants, such as talc, silicon dioxide, stearic acid, sodium stearyl fumarate or magnesium stearate; and if desired, with diluents, buffering agents, moistening agents, preservatives and flavoring agents.

In some embodiments, the unit dosage form or pharmaceutical composition comprises 25, 50, 75, or 100 mg lonafarnib or a pharmaceutically acceptable salt thereof. In some embodiments, the unit dosage form or pharmaceutical composition comprises 25 mg lonafarnib or a pharmaceutically acceptable salt thereof. In some embodiments, the unit dosage form or pharmaceutical composition comprises 50 mg lonafarnib or a pharmaceutically acceptable salt thereof. In some embodiments, the unit dosage form or pharmaceutical composition comprises 75 mg lonafarnib or a pharmaceutically acceptable salt thereof. In some embodiments, the unit dosage form or pharmaceutical composition comprises 100 mg lonafarnib or a pharmaceutically acceptable salt thereof.

In some embodiments, the unit dosage form or pharmaceutical composition comprises 50, 75 or 100 mg ritonavir, or a pharmaceutically acceptable salt thereof. In some embodiments, the unit dosage form or pharmaceutical composition comprises 50 mg ritonavir, or a pharmaceutically acceptable salt thereof. In some embodiments, the unit dosage form or pharmaceutical composition comprises 75 mg ritonavir, or a pharmaceutically acceptable salt thereof. In some embodiments, the unit dosage form or pharmaceutical composition comprises 100 mg ritonavir, or a pharmaceutically acceptable salt thereof. In some embodiments, for each of these types of unit dosage forms having 50 mg, 75 mg, or 100 mg ritonavir, novel dosage forms are provided in which the lonafarnib is provided at 25 mg, 50 mg, 75 mg, or 100 mg.

In some embodiments, the unit dosage form or pharmaceutical composition is for administration twice daily (BID). For example, any of the dosage forms in which the lonafarnib is provided at 25 mg, 50 mg, 75 mg, or 100 mg may be administered BID.

In some embodiments, the unit dosage form or pharmaceutical composition is for administration once daily (QD). For example, any of the dosage forms in which the lonafarnib is provided at 25 mg, 50 mg, 75 mg, or 100 mg may be administered QD.

In some embodiments, the unit dosage form or pharmaceutical composition comprises 100 mg lonafarnib or a pharmaceutically acceptable salt thereof and 50 mg ritonavir or a pharmaceutically acceptable salt thereof, and is for administration BID.

In some embodiments, the unit dosage form or pharmaceutical composition comprises 100 mg lonafarnib or a pharmaceutically acceptable salt thereof and 75 mg ritonavir or a pharmaceutically acceptable salt thereof, and is for administration BID.

In some embodiments, the unit dosage form or pharmaceutical composition comprises 100 mg lonafarnib or a pharmaceutically acceptable salt thereof and 100 mg ritonavir or a pharmaceutically acceptable salt thereof, and is for administration BID.

In some embodiments, the unit dosage form or pharmaceutical composition comprises 100 mg lonafarnib or a pharmaceutically acceptable salt thereof and 50 mg ritonavir or a pharmaceutically acceptable salt thereof, and is for administration QD.

In some embodiments, the unit dosage form or pharmaceutical composition comprises 100 mg lonafarnib or a pharmaceutically acceptable salt thereof and 75 mg ritonavir or a pharmaceutically acceptable salt thereof, and is for administration QD.

In some embodiments, the unit dosage form or pharmaceutical composition comprises 100 mg lonafarnib or a pharmaceutically acceptable salt thereof and 100 mg ritonavir or a pharmaceutically acceptable salt thereof, and is administered QD.

In some embodiments, the unit dosage form or pharmaceutical composition comprises 75 mg lonafarnib or a pharmaceutically acceptable salt thereof and 50 mg ritonavir or a pharmaceutically acceptable salt thereof, and is for administration BID.

In some embodiments, the unit dosage form or pharmaceutical composition comprises 75 mg lonafarnib or a pharmaceutically acceptable salt thereof and 75 mg ritonavir or a pharmaceutically acceptable salt thereof, and is for administration BID.

In some embodiments, the unit dosage form or pharmaceutical composition comprises 75 mg lonafarnib or a pharmaceutically acceptable salt thereof and 100 mg ritonavir or a pharmaceutically acceptable salt thereof, and is for administration BID.

In some embodiments, the unit dosage form or pharmaceutical composition comprises 75 mg lonafarnib or a pharmaceutically acceptable salt thereof and 50 mg ritonavir or a pharmaceutically acceptable salt thereof, and is for administration QD.

In some embodiments, the unit dosage form or pharmaceutical composition comprises 75 mg lonafarnib or a pharmaceutically acceptable salt thereof and 75 mg ritonavir or a pharmaceutically acceptable salt thereof, and is for administration QD.

In some embodiments, the unit dosage form or pharmaceutical composition comprises 75 mg lonafarnib or a pharmaceutically acceptable salt thereof and 100 mg ritonavir or a pharmaceutically acceptable salt thereof, and is administered QD.

In some embodiments, the unit dosage form or pharmaceutical composition comprises 50 mg lonafarnib or a pharmaceutically acceptable salt thereof and 50 mg ritonavir or a pharmaceutically acceptable salt thereof, and is for administration BID.

In some embodiments, the unit dosage form or pharmaceutical composition comprises 50 mg lonafarnib or a pharmaceutically acceptable salt thereof and 75 mg ritonavir or a pharmaceutically acceptable salt thereof, and is for administration BID.

In some embodiments, the unit dosage form or pharmaceutical composition comprises 50 mg lonafarnib or a pharmaceutically acceptable salt thereof and 100 mg ritonavir or a pharmaceutically acceptable salt thereof, and is for administration BID.

In some embodiments, the unit dosage form or pharmaceutical composition comprises 50 mg lonafarnib or a pharmaceutically acceptable salt thereof and 50 mg ritonavir or a pharmaceutically acceptable salt thereof, and is for administration QD.

In some embodiments, the unit dosage form or pharmaceutical composition comprises 50 mg lonafarnib or a pharmaceutically acceptable salt thereof and 75 mg ritonavir or a pharmaceutically acceptable salt thereof, and is for administration QD.

In some embodiments, the unit dosage form or pharmaceutical composition comprises 50 mg lonafarnib or a pharmaceutically acceptable salt thereof and 100 mg ritonavir or a pharmaceutically acceptable salt thereof, and is administered QD.

In some embodiments, the unit dosage form or pharmaceutical composition comprises 25 mg lonafarnib or a pharmaceutically acceptable salt thereof and 50 mg ritonavir or a pharmaceutically acceptable salt thereof, and is for administration BID.

In some embodiments, the unit dosage form or pharmaceutical composition comprises 25 mg lonafarnib or a pharmaceutically acceptable salt thereof and 75 mg ritonavir or a pharmaceutically acceptable salt thereof, and is for administration BID.

In some embodiments, the unit dosage form or pharmaceutical composition comprises 25 mg lonafarnib or a pharmaceutically acceptable salt thereof and 100 mg ritonavir or a pharmaceutically acceptable salt thereof, and is for administration BID.

In some embodiments, the unit dosage form or pharmaceutical composition comprises 25 mg lonafarnib or a pharmaceutically acceptable salt thereof and 50 mg ritonavir or a pharmaceutically acceptable salt thereof, and is for administration QD.

In some embodiments, the unit dosage form or pharmaceutical composition comprises 25 mg lonafarnib or a pharmaceutically acceptable salt thereof and 75 mg ritonavir or a pharmaceutically acceptable salt thereof, and is for administration QD.

In some embodiments, the unit dosage form or pharmaceutical composition comprises 25 mg lonafarnib or a pharmaceutically acceptable salt thereof and 100 mg ritonavir or a pharmaceutically acceptable salt thereof, and is for administration QD.

In some embodiments, the unit dosage form or pharmaceutical composition comprising lonafarnib or a pharmaceutically acceptable salt thereof and ritonavir or a pharmaceutically acceptable salt thereof is formulated as a delayed release formulation. Methods for making controlled or delayed release formulations are well known in the art. As a non-limiting example, a unit dosage form or pharmaceutical composition can be formulated as a core comprising the amorphous co-precipitate which is coated by one or more layers comprising one or more materials that delay release of the drug. For example, the coating may comprise one or more of a polymer or copolymer of acrylic acid, methacrylic acid etc. (e.g. Eudragits or Carbopol), cellulose derivatives such as hydroxypropylmethylcellulose, hydroxypropylcellulose, carboxymethylcellulose, ethylcellulose, cellulose acetate, polyvinyl alcohol, polyethylene glycol, salts of higher fatty acids, or esters of monohydric or polyhydric alcohols with short-, medium- or long-chain, saturated or unsaturated fatty acids.

In one embodiment, the unit dosage form or pharmaceutical composition comprises an enteric release agent (e.g., as a layer or coating) that allows the release of the drug upon exposure to a characteristic aspect of the gastrointestinal tract. In an embodiment, the enteric release agent is pH-sensitive and is affected by changes in pH encountered within the gastrointestinal tract (pH sensitive release). The enteric material typically remains insoluble at gastric pH, then allows for release of the active ingredient in the higher pH environment of the downstream gastrointestinal tract (e.g., often the duodenum, or sometimes the colon). In another embodiment, the enteric material comprises enzymatically degradable polymers that are degraded by bacterial enzymes present in the lower gastrointestinal tract, particularly in the colon. Optionally, the unit dosage form is formulated with a pH-sensitive enteric material designed to result in a release within about 0.25-2 hours when at or above a specific pH. In various embodiments, the specific pH can for example be about 4.5, 5, 5.5, 6, or 6.5. In particular embodiments, the pH-sensitive material allows release of at least 80% of the drug within 1 hour when exposed to a pH of about 5.5 or higher. In another embodiment, the pH-sensitive material allows release of at least 80% of the drug within 1 hour when exposed to a pH of about 6 or higher. Materials used for enteric release formulations, for example as coatings, are well known in the art, for example, those described in U.S. Pat. Pub. No. 2011/0313009. Combinations of different enteric materials may also be used. Multi-layer coatings using different polymers may also be applied.

V. Methods of Treatment

Also provided are methods for treating diseases relating to HDV infection, in which the HDV-infected patient is treated by orally administering an amorphous co-precipitate of lonafarnib and ritonavir or a unit dosage form or pharmaceutical composition comprising an amorphous co-precipitate of lonafarnib and ritonavir. In some embodiments, the method comprises a method of treating a HDV infection in a human. In some embodiments, the method comprises a method of reducing hepatitis delta virus ribonucleic acid (HDV-RNA) in a human infected with HDV. In some embodiments, the lonafarnib and ritonavir co-precipitates, unit dosage forms, and/or pharmaceutical compositions are administered according to doses and dosing schedules described herein. In some embodiments the HDV-infected patient also is administered one or more additional therapeutic agents, e.g., one or more classes of gastrointestinal (GI) modifying agents and/or one or more antiviral agents (e.g., interferons).

In certain embodiments, the co-precipitate, unit dosage form, or pharmaceutical composition is administered according to a schedule that results in the serum lonafarnib levels greater than 2,000 ng/ml, preferably greater than 4,000 ng/ml, more preferably in the range of about 3,500 ng/ml to about 7,500 ng/ml (e.g., about 4,500 ng/ml to about 5,500 ng/ml, about 5,000 ng/ml to about 6,000 ng/ml, about 5,500 ng/ml to about 6,500 ng/ml, about 6,000 ng/ml to about 7,000 ng/ml, or about about 6,500 ng/ml to about 7,500 ng/ml) or about 5,000 ng/ml to about 7,000 ng/ml.

Serum levels of lonafarnib can be measured using art-known methods. As used herein, a serum lonafarnib level or concentration can be measured from a serum sample obtained from a subject periodically (such as weekly, biweekly, monthly or according to other schedules) and the levels during intervening periods can be extrapolated. For example, if a measurement of 4,000 ng/ml is obtained at 4 weeks and a measurement of 6,000 ng/ml is obtained at 6 weeks, for purposes of this analysis it is concluded that the serum level during the intervening two weeks ranged between 4,000 and 6,000 ng/ml. In some embodiments the first measurement is made no earlier than one week after the initiation of oral therapy.

In one embodiment the patient receiving the lonafarnib-ritonavir co-therapy with a co-precipitate, unit dosage form, or pharmaceutical composition as described herein receives lonafarnib at a daily dose of 50 mg per day to 200 mg per day, for example 50 mg per day, 75 mg per day, 100 mg per day, 150 mg per day, or 200 mg per day, and receives ritonavir at a daily dose of 50 mg to 200 mg per day, for example 50 mg per day, 75 mg per day, 100 mg per day, 150 mg per day, or 200 mg per day. The aforementioned doses can be achieved by administering the lonafarnib-ritonavir co-therapy OD or BID.

Patients may receive lonafarnib-ritonavir co-therapy with a co-precipitate, unit dosage form, or pharmaceutical composition as described herein fora predetermined time, an indefinite time, or until an endpoint is reached. Treatment may be continued on a continuous daily basis for at least two to three months. Therapy is typically for at least 30 days, more often at least 60 days or at least 90 days, even more often at least 120 days, sometimes for at least 150 days, and sometimes for at least 180 days. In some embodiments, treatment is continued for at least six months, nine months, one year, or longer. In other embodiments, treatment is continued for the rest of the patient's life or until administration is no longer effective in maintaining the virus at a sufficiently low level to provide meaningful therapeutic benefit.

In some embodiments, therapy as disclosed herein is continued for a period of time until HDV-RNA levels are below 3 log HDV-RNA copies/mL (below 1,000 copies/mL), or sometimes until HDV-RNA levels are below 2 log HDV-RNA copies/mL (below 100 copies/mL) or below the level of detection. In some cases therapy may be continued fora period of time (such as 1 to 3 months or longer) after viral load has dropped to acceptably low levels (e.g., undetectable levels).

In some embodiments, the pharmaceutically acceptable compositions or pharmaceutical formulations and unit dose forms described herein are used in combination with gastrointestinal modifying therapies. Agents for treatment of gastrointestinal irritations include, but are not limited to, anti-emetics, antacids (H2-receptor antagonists and proton pump inhibitors) and anti-diarrheals. Exemplary agents (for illustration and not limitation) are listed in TABLE 1 below. In one approach, GI modifying agents are administered prior to administration of the lonafarnib-ritonavir co-therapy. In another approach, the lonafarnib-ritonavir co-therapy and GI modifying agents are administered at the same time.

TABLE 1

Exemplary GI Modifying Agents

| Class | Exemplary agents |
|---|---|
| Antiemetics | 5-HT$_3$ antagonists (such as ondansetron (Zofran ®), tropisetron (Navoban ®), granisetron (Kytril ®), palonosetron (Aloxi ®), and dolasetron (Anzemet ®)) and NK1 receptor antagonists (such as aprepritant (Emend ®), casopitant, and fosaprepitant (Emend ® IV)), and combined 5-HT3 antagonist and NK1 receptor antagonist (such as netiputant/palonosetron (Akynzeo ®). |
| Antacids | H2-receptor antagonists (such as ranitidine (Zantac ®), famotidine (Pepcid ®), cimetidine (Tagamet ®) and nizatidine (Axid ®) and Proton pump inhibitors (such as omeprazole (Prilosec ®), omeprazole/sodium bicarbonate (Zegerid ®), esomeprazole magnesium (Nexium ®), esomeprazole strontium, lansoprazole (Prevacid ®), dexlansoprazole (Dexilant ®), and pantoprazole sodium (Protonix ®)). |
| Anti-diarrheals | atropine/diphenoxylate (Lomotil ®, Lonox ®), loperamide HCl (Imodium ®), and bismuth subsalicylate (Kaopectate ®, Pepto-Bismol ®). |

It is contemplated that HDV-infected patients receiving lonafarnib-ritonavir co-therapy with a co-precipitate, unit dosage form, or pharmaceutical composition as described herein may also be treated with antiviral agents such as interferons, nucleosides and nucleotide analogues, compounds used to treat HBV infections, or other agents. In some embodiments, a lonafarnib-ritonavir amorphous co-precipitate, unit dosage form, or pharmaceutical composition as described herein is administered in combination with an interferon. Suitable interferons include, but are not limited to pegylated IFN-α-2a, pegylated IFN-α-2b, consensus IFN, IFN-λ, and pegylated IFN-λ.

The term "interferon-alpha" or "IFN-α" and "interferon-lambda" or "IFN-λ" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α. The term "IFN-α" also encompasses consensus IFN-α. Thus, essentially any IFN-α or IFN-λ that has antiviral properties, as described for naturally occurring IFN-α, can be used in the combination therapies described herein. The term "IFN-α" encompasses derivatives of IFN-α that are derivatized (e.g., are chemically modified relative to the naturally occurring peptide) to alter certain properties such as serum half-life. As such, the term "IFN-α" includes IFN-α derivatized with polyethylene glycol ("PEGylated IFN-α"), and the like. PEGylated IFN-α, and methods for making same, are discussed in, e.g., U.S. Pat. Nos. 5,382, 657; 5,951,974; and 5,981,709. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha-2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, CA).

The term "interferon-lambda" or "IFN-λ" as used herein includes naturally occurring IFN-λ; synthetic IFN-λ; derivatized IFN-λ (e.g., PEGylated IFN-λ, glycosylated IFN-λ, and the like); and analogs of naturally occurring or synthetic IFN-λ. In some embodiments, an IFN-λ is a derivative of IFN-λ that is derivatized (e.g., chemically modified relative to the naturally occurring peptide) to alter certain properties such as serum half-life. As such, the term "IFN-λ" includes IFN-λ derivatized with polyethylene glycol ("PEGylated IFN-λ"), and the like. IFN-λ, including PEGylated IFN-λ (e.g., PEGylated IFN-λ-1a), and methods for making same, are discussed in, e.g., U.S. Pat. Nos. 6,927,040, 7,038,032, 7,135,170, 7,157,559, 7,595,174, 7,759,092, 7,968,315, 8,211,670, 8,759,027, and 8,980,245; and PCT publication Nos. WO 05/097165, WO 07/012,033, WO 07/013,944 and WO 07/041,713; all of which are herein incorporated by reference in their entirety.

In some embodiments, an interferon (e.g., pegylated IFN alfa 2a, pegylated IFN alfa 2b, pegylated IFN-λ1 (e.g., pegylated IFN-λ-1a), pegylated IFN-λ-2, or pegylated IFN-λ-3) is administered in an amount of 80 mcg QW, 120 mcg QW, or 180 mcg QW. Administration can be continuous for about 30 days, more typically 30 or 60 days, and often as long 6 months, 9 months, and 12 months.

EXAMPLES

The following examples are offered to illustrate, but not to limit, the claimed invention.

Reference Example 5.0 gram of ritonavir and 5.0 gram of povidone were dissolved in 300 mL of dichloromethane by stirring at room temperature. The solution was spray dried using a Model GB22 Yamato Lab Spray Dryer with the following operating parameters: internal nozzle diameter 711 μm; pump rate 12-14 mL/min; inlet temperature 60° C.; outlet temperature NMT 45° C.; atomization air pressure 0.15 MPa and air flow 0.5 m³/min. For 10 g of solids in the spray solution, 3.7 g were collected in the receiving flask for a yield of 37%. The components of the ritonavir-povidone (1:1) spray solution are shown in Table 2.

TABLE 2

Ritonavir- Povidone (1:1) Spray Solution

| Item | Ingredient name | w/w % dry basis | qty/batch |
|---|---|---|---|
| a | Ritonavir | 50.0 | 5.0 g |
| b | Povidone | 50.0 | 5.0 g |
| c | Dichloromethane | | 300 mL |
| | Total: | 100.0 | 10.0 g (solid)* |

*Total solids in the spray-solution 3% (w/v)

Example 1. Preparation of Ritonavir-Lonafarnib-Copolymer Co-Precipitates

1:1:2 Co-Precipitate 5.0 gram of Ritonavir, 5.47 gram of lonafarnib, and 10.0 gram of Povidone K30 were dissolved in 600 mL of dichloromethane by stirring at room temperature. The solution was spray dried using a Model GB22 Yamato Lab Spray Dryer with the following operating parameters: internal nozzle diameter 711 μm; pump rate 12-14 mL/min; inlet temperature 60° C.; outlet temperature NMT 45° C.; atomization air pressure 0.15 MPa and air flow 0.5 m³/min. For 20.47 g of solids in the spray solution, 15.9 g were collected in the receiving flask for a yield of 77%. The components of the ritonavir-lonafarnib-povidone (1:1:2) spray solution are shown in Table 3.

TABLE 3

Ritonavir- Lonafarnib - Povidone (1:1:2) Spray Solution

| Item | Ingredient name | w/w % dry basis | qty/batch |
|---|---|---|---|
| a | Ritonavir (RTN) | 25.0 | 5.00 |
| b | Lonafarnib (LNF) | 25.0 | 5.47* |
| c | Povidone K30 | 50.0 | 10.00 |
| d | Dichloromethane | | 600 mL |
| | Total: | 100.0 | 20.47 g (solid)** |

*HPLC assay was 91.4%
**Total solids in the spray-solution 3% (w/v)

1:2:3 Co-Precipitate 6.5 gram of the ritonavir-lonafarnib-povidone (1:1:2) co-precipitate (which corresponds to 1.6 gram of ritonavir, 1.6 gram lonafarnib, and 3.3 gram of povidone K30), an additional 1.6 gram of ritonavir and an additional 1.5 gram of povidone K30 were dissolved in 300 mL of dichloromethane by stirring at room temperature. The solution was spray dried using a Model GB22 Yamato Lab Spray Dryer with the following operating parameters: internal nozzle diameter 711 μm; pump rate 12-14 mL/min; inlet temperature 60° C.; outlet temperature NMT 45° C.; atomization air pressure 0.15 MPa and air flow 0.5 m³/min. For 9.6 g of solids in the spray solution, 5.6 g were collected in the receiving flask for a yield of 58%. The components of the ritonavir-lonafarnib-povidone (1:2:3) spray solution are shown in Table 4.

TABLE 4

Ritonavir- Lonafarnib - Povidone (1:2:3) Spray Solution

| Item | Ingredient name | w/w % dry basis | qty/batch |
|---|---|---|---|
| a | RTN | 34.0 | 1.6* + 1.6 = 3.2 |
| b | LNF | 17.0 | 1.6* |
| c | Povidone K30 | 49.0 | 3.3* + 1.5 = 4.8 |
| d | Dichloromethane | | 300 mL |
| | Total: | 100.0 | 9.6 g (solid)** |

*quantity from 6.5 gram of 1:1:2 co-precipitate
**Total solids in the spray-solution 3% (w/v)

1:1:5 Co-Precipitate 7.5 gram of the ritonavir-lonafarnib-providone (1:1:2) co-precipitate (which corresponds to 1.9 gram of ritonavir, 1.9 gram lonafarnib, and 3.8 gram of povidone K30), and an additional 5.0 gram of povidone K30 were dissolved in 390 mL of dichloromethane by stirring at room temperature. The solution was spray dried using a Model GB22 Yamato Lab Spray Dryer with the following operating parameters: internal nozzle diameter 711 μm; pump rate 12-14 mL/min; inlet temperature 60° C.; outlet temperature NMT 45° C.; atomization air pressure 0.15 MPa and air flow 0.5 m³/min. For 12.5 g of solids in the spray solution, 8.8 g were collected in the receiving flask for a yield of 70%. The components of the ritonavir-lonafarnib-povidone (1:1:5) spray solution are shown in Table 5.

TABLE 5

Ritonavir- Lonafarnib - Povidone (1:1:5) Spray Solution

| Item | Ingredient name | w/w % dry basis | qty/batch |
|---|---|---|---|
| a | RTN | 15.0 | 1.9* |
| b | LNF | 15.0 | 1.9* |
| c | Povidone K30 | 70.0 | 3.8* + 5.0 = 8.8 |
| d | Dichloromethane | | 390 mL |
| | Total: | 100.0 | 12.5 g (solid)** |

*quantity from 7.5 gram of 1:1:2 co-precipitate
**Total solids in the spray-solution 3% (w/v)

1:1:2 Co-Precipitate with HPMC Polymer 2.5 gram of Ritonavir, 2.61 gram of lonafarnib, and 5.0 gram of hydroxymethylcellulose (HPMC) were dissolved in 340 mL of dichloromethane by stirring at room temperature. The solution was spray dried using a Model GB22 Yamato Lab Spray Dryer with the following operating parameters: internal nozzle diameter 711 μm; pump rate 12-14 mL/min; inlet temperature 60° C.; outlet temperature NMT 45° C.; atomization air pressure 0.15 MPa and air flow 0.5 m³/min. For 10.1 g of solids in the spray solution, 7.2 g were collected in the receiving flask for a yield of 71%. The components of the ritonavir-lonafarnib-HPMC (1:1:2) spray solution are shown in Table 6.

TABLE 6

Ritonavir- Lonafarnib - HPMC (1:1:2) Spray Solution

| Item | Ingredient name | w/w % dry basis | qty/batch |
|---|---|---|---|
| a | Ritonavir (RTN) | 25.0 | 2.50 |
| b | Lonafarnib (LNF) | 25.0 | 2.61* |
| c | HPMC | 50.0 | 5.00 |
| d | Dichloromethane | | 340 mL |
| | Total: | 100.0 | 10.1 g (solid)** |

*HPLC assay was 95.8%
**Total solids in the spray-solution 3% (w/v)

The amorphous state of each co-precipitate was verified by X-ray powder diffraction (XRPD). The diffraction pattern was verified by X-ray diffraction using a Bruker D2 Phaser X-ray diffractometer with Lynxeye detector, Cu Kα radiation ($\lambda=1.5406$ Å). Acquisition was done over a range of 5-55° 2θ, increment of 0.05° 2θ, 1.0 s step time and 0.6 mm opening slit and a 2.5 mm detector windows. The samples were analyzed using a low volume sample holder and kept under a constant rotation of 15 rpm during the analysis. FIG. 1A is a powder X-ray pattern of the amorphous 1:1:2, 1:2:3, and 1:1:5 co-precipitates with povidone as the co-polymer. Consistent with the characteristic of amorphous solid form, the amorphous 1:1:2, 1:2:3, and 1:1:5 co-precipitates do not exhibit crystalline diffraction peaks. The amorphous 1:1:2 co-precipitate with HPMC also does not exhibit crystalline diffraction peaks (data not shown).

Residual solvent from spray-dried material was verified by thermogravimetric analysis (TGA). The analysis was performed using a TA Instrument Q50 thermogravimetric analyzer at scanning speed of 10° C. min$^{-1}$ over a temperature range of 25 to 200° C. The samples were heated in a platinum open pan under nitrogen purge (60 mL min$^{-1}$).

Figure 2A:
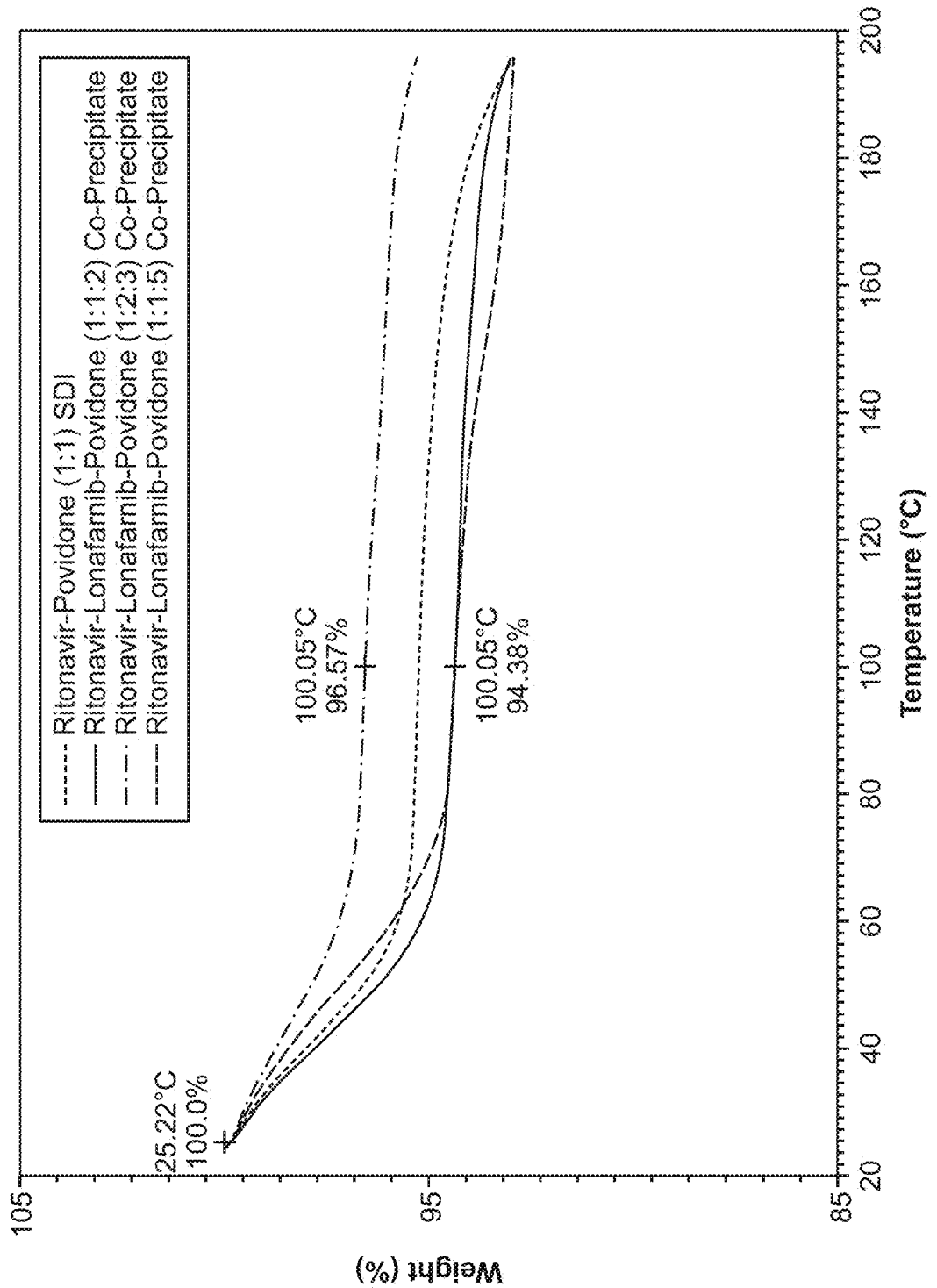
FIG. 2A-B. Thermogravimetric analysis (TGA). (A) Characteristic powder TGA thermogram of ritonavir-povidone (1:1) and ritonavir-lonafarnib-povidone (1:1:2), (1:2:3), and (1:1:5) co-precipitates prepared as described in Example 1. (B) Characteristic powder TGA thermogram comparing ritonavir-lonafarnib-povidone (1:1:2) and ritonavir-lonafarnib-HPMC (1:1:2) co-precipitates prepared as described in Example 1.

FIG. 2A illustrates the sample weight (in percent of original weight) as a function of temperature. This material exhibited distinct weight-loss steps. The first step (weight loss 4.8-5.6%) at temperatures between 25 and 100° C. corresponds to loss of volatile compounds (water and dichloromethane) followed by material decomposition initiated at approximately 180° C. Identification and quantification of residual solvents using more sophisticated techniques such gas chromatography should be employed to ensure compliance with ICH Q3C guidelines.

Figure 2B:
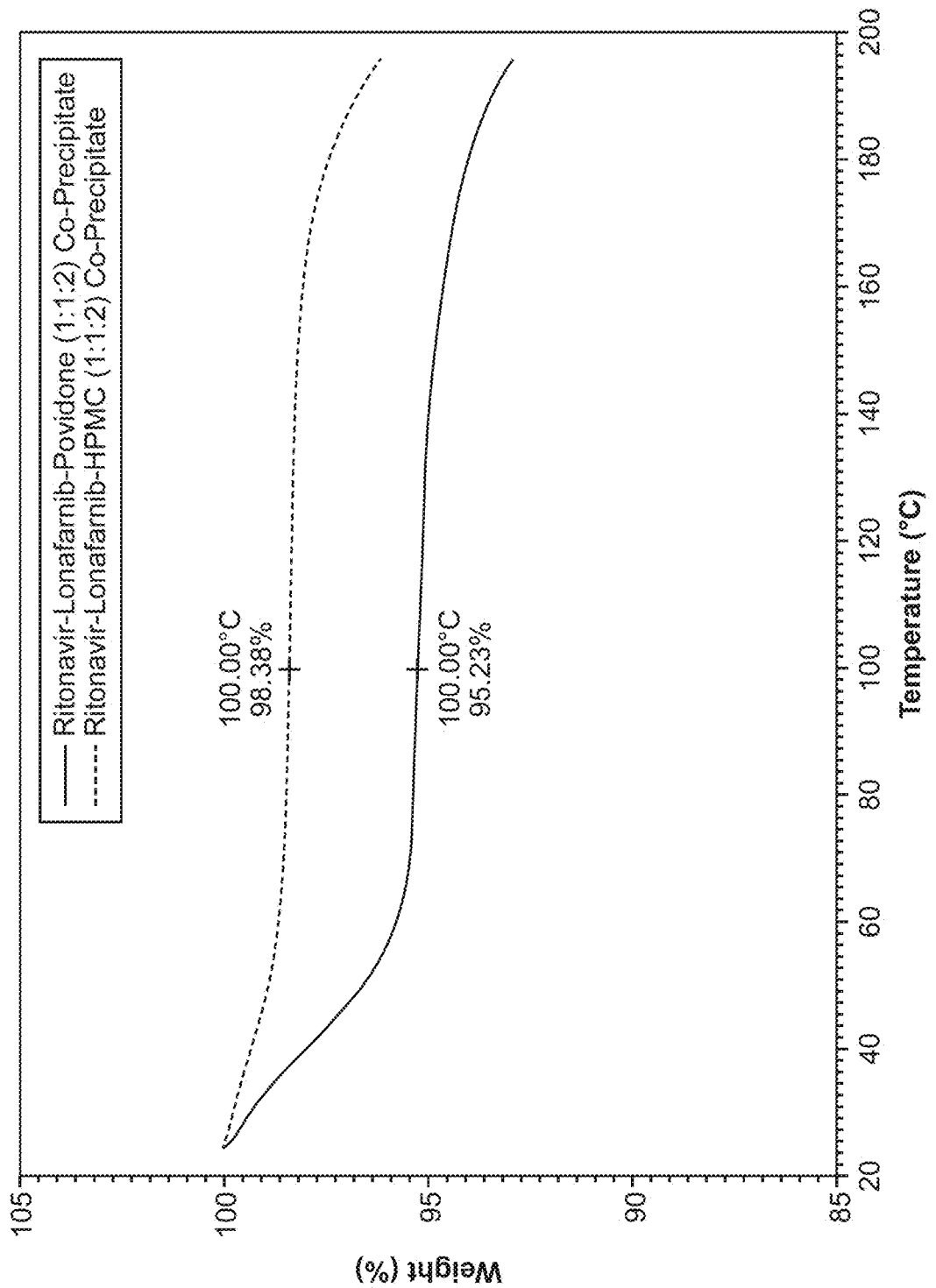

FIG. 2B compares samples with similar API (active pharmaceutical ingredient) compositions but different polymers, a 1:1:2 Ritonavir-Lonafarnib-Povidone containing sample and a 1:1:2 Ritonavir-Lonafarnib-HPMC containing sample. As shown in FIG. 2B, the HPMC containing sample contains 1.7% of volatiles, much lower compared to the povidone containing sample at 4.8%. This difference is likely linked to higher hygroscopicity and/or dichloromethane affinity of povidone versus HPMC.

The amorphous co-precipitates were characterized by bulk/tapped density and powder flow properties. Bulk and tapped densities were determined using the USP <616> method with a Vanderkamp tap density tester model 10700 by measuring the volume of a known mass of powder sample in a graduated cylinder while the tapped density was measured by mechanically tapping the measuring cylinder until no further volume change was observed. The powder flow properties were evaluated using the Carr's Compressibility Index and Hausner ratio. The Compressibility Index and Hausner ratio values interpretation as per USP <1174> as well as a descriptive qualitative example are presented in Table 7.

Compressibility Index=(Tapped density−Bulk density)/Tapped density×100%

Hausner Ratio=Tapped density/Bulk density

TABLE 7

Scale of Flowability

| Compressibility Index (%) | Flow Character | Hausner Ratio | Example |
|---|---|---|---|
| <10 | Excellent | 1.00-1.11 | Free-flowing granules |
| 11-15 | Good | 1.12-1.18 | Powdered granules |
| 16-20 | Fair | 1.19-1.25 | Coarse powders |
| 21-25 | Passable | 1.26-1.34 | Fine powders |
| 26-31 | Poor | 1.35-1.45 | Fluidizable powders |
| 32-37 | Very poor | 1.46-1.59 | Cohesive powders |
| >38 | Very, very poor | >1.60 | Very cohesive powders |

Powder flow properties and yield spray-dried material were different for each lot. Ritonavir spray dried intermediate showed Carr's Index ≤20% and Hausner Ratio ≤1.25 which are typical of powder having fair flowability. Table 8 presents the powder flow properties. For the co-precipitates containing povidone, powder density values were low but showed acceptable poor to very very poor powder flow. The co-precipitates containing HPMC showed increased values of density with all of the spray-dried material retrieved from the collection vessel.

TABLE 8

Density and Flow Properties

|  | Test# | Density Parameters | | Flow Properties | | |
|---|---|---|---|---|---|---|
|  |  | Bulk (g/cm³) | Tapped (g/cm³) | Carr's Index (%) | Hausner Ratio | Flowability |
| Ritonavir-Povidone (1:1) Co-precipitate | 1 | 0.205 | 0.253 | 19 | 1.23 | Fair |
|  | 2 | 0.205 | 0.257 | 20 | 1.25 |  |
| Ritonavir-Lonafarnib-Povidone (1:1:2) Co-Precipitate | 1 | 0.134 | 0.208 | 36 | 1.55 | Very poor |
|  | 2 | 0.135 | 0.207 | 34 | 1.53 |  |
| Ritonavir-Lonafarnib-Povidone (1:2:3) Co-Precipitate | 1 | 0.199 | 0.286 | 30 | 1.44 | Poor/Very poor |
|  | 2 | 0.200 | 0.294 | 32 | 1.47 |  |
| Ritonavir-Lonafarnib-Povidone (1:1:5) Co-Precipitate | 1 | 0.184 | 0.300 | 39 | 1.63 | Very very poor |
|  | 2 | 0.191 | 0.311 | 39 | 1.63 |  |
| Ritonavir-Lonafarnib-HPMC (1:1:2) Co-Precipitate | 1 | 0.343 | 0.556 | 38 | 1.62 | Very poor |
|  | 2 | 0.344 | 0.551 | 38 | 1.60 |  |

Example 2. Treatment of HDV Patients with 100 mg BID Lonafarnib and 100 mg QD Ritonavir This example describes the treatment of HDV-infected patients using separately formulated lonafarnib and ritonavir. Three human subjects known to be infected with HDV, as documented by baseline HDV-RNA viral titers ranging from 5.14 log HDV-RNA copies/mL to 6.83 log HDV-RNA copies/mL and alanine aminotransferase (ALT) values of 84-195 U/L, were administered lonafarnib-ritonavir co-therapy comprising a lonafarnib formulation orally administered at a dose of 100 mg BID and a ritonavir formulation orally administered at a dose of 100 mg QD for a period of 28 days (1 month).

Figure 3:
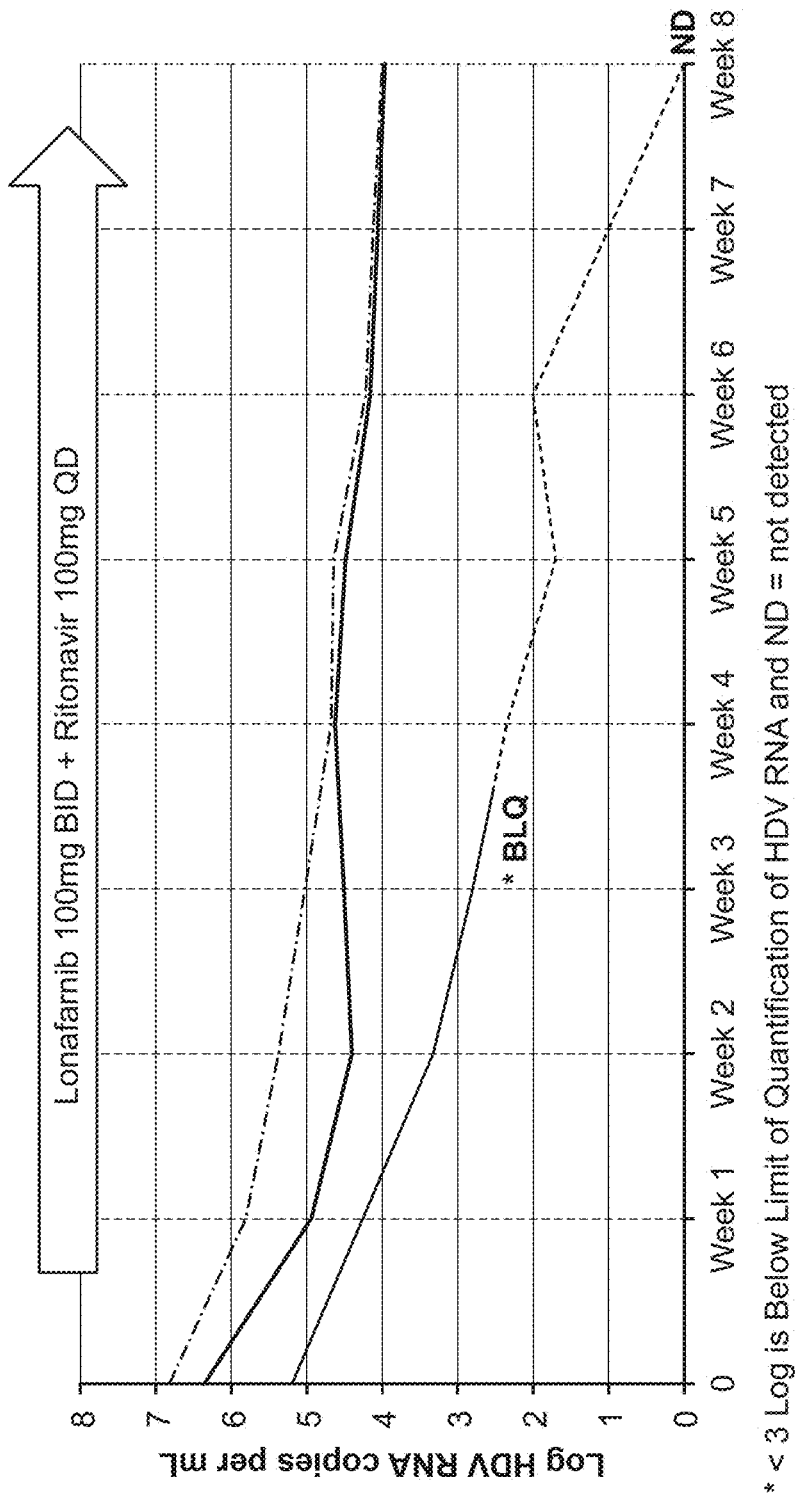
FIG. 3. HDV-RNA viral titers in human patients treated with separately formulated lonafarnib and ritonavir, in which lonafarnib was administered at a dose of 100 mg BID and ritonavir was administered at a dose of 100 mg QD for a period of 28 days, as described in Example 2.

At the end of the treatment period, all three subjects' HDV-RNA viral titers had decreased from baseline, ranging from −1.95 log HDV-RNA copies/mL to at least −2.2 log HDV-RNA copies/mL drop in HDV-RNA, with an average drop across the three subjects of −2.1 log HDV-RNA copies/mL. The change in HDV-RNA viral load for each patient was calculated and is shown in Table 9 and FIG. 3. In addition, all three subjects' ALT values decreased from baseline, ranging from 35-50 U/L, as shown in Table 9. Upper limit of normal for ALT values is estimated to be 40 U/L.

TABLE 9

Administration of 100 mg lonafarnib BID + 100 mg ritonavir QD

| Patient | Log HDV RNA copies/mL | | | | | | | | ALT (IU/L)* |
|---|---|---|---|---|---|---|---|---|---|
|  | Baseline | Wk 1 | Wk 2 | Wk 4 | Wk 5 | Wk 6 | Wk 8 | Change | Day 1 to Day 28 to Day 56 |
| 1 | 6.34 | 4.96 | 4.40 | 4.63 | 4.48 | 4.18 | 3.97 | −2.37 | 83→50→43 |
| 2 | 5.14 | 4.21 | 3.30 | 2.38 | 1.86 | 2.08 | ND** | >−5 | 206→58→32 |
| 3 | 6.83 | 5.82 | 5.38 | 4.68 | 4.62 | 4.23 | 3.99 | −2.84 | 72→35→43 |

*Upper limit of normal = 40 IU/L
**Be low detection limit.

The data show that therapy with separately-formulated lonafarnib and ritonavir is efficacious for treating patients infected with HDV. Administration of a unit dosage form comprising both lonafarnib and ritonavir as provided herein should be similarly efficacious for treating patients infected with HDV.

Example 3. Treatment of HDV Patients with Lonafarnib and Ritonavir

This example describes the anti-HDV effect of combination therapy with separately formulated lonafarnib and ritonavir at several combinations of dosages. Eight patients with chronic HDV infection were divided into four groups and treated with different dose combinations of separately formulated lonafarnib and ritonavir (orally administered) for 42 days under the regimens summarized in Table 10. The patients were followed for an additional period of time after discontinuation of therapy.

Results

Patients 1-7 responded to therapy, as defined by greater than or equal to a 1 log HDV-RNA copies/mL decline in HDV-RNA levels during treatment. The changes in Group 1 patients' HDV-RNA levels from baseline to as a result of lonafarnib and ritonavir combination therapy are summarized in Table 10.

TABLE 10

Lonafarnib-Ritonavir Co-therapy

| Group | Patient 1 | Patient 2 | Patient 3 | Patient 4 | Patient 5 | Patient 6 | Patient 7 | Patient 8 |
|---|---|---|---|---|---|---|---|---|
| | Group 1 | | Group 2 | | Group 3 | Group 4 | | |
| Dose lonafarnib | 100 mg BID | | 100 mg BID | | 100 mg QD | 150 mg QD | | |
| Dose ritonavir | 100 mg QD | | 50 mg QD | | 100 mg QD | 100 mg QD | | |
| Change log VL Baseline to Nadir | −2.15 | −3.70 | −2.05 | −2.02 | −3.18 | −2.58 | −1.79 | −0.70 |
| Change log VL Baseline to Week 6 | −2.15 | −3.70 | −2.05 | −1.49 | −2.42 | −1.74 | −1.79 | −0.52 |
| LNF Serum Concentration at Week 6 (ng/mL) | 2966 | 6397 | 4025 | 3044 | 2336 | 1640 | 1841 | 1830 |

Figure 4A:
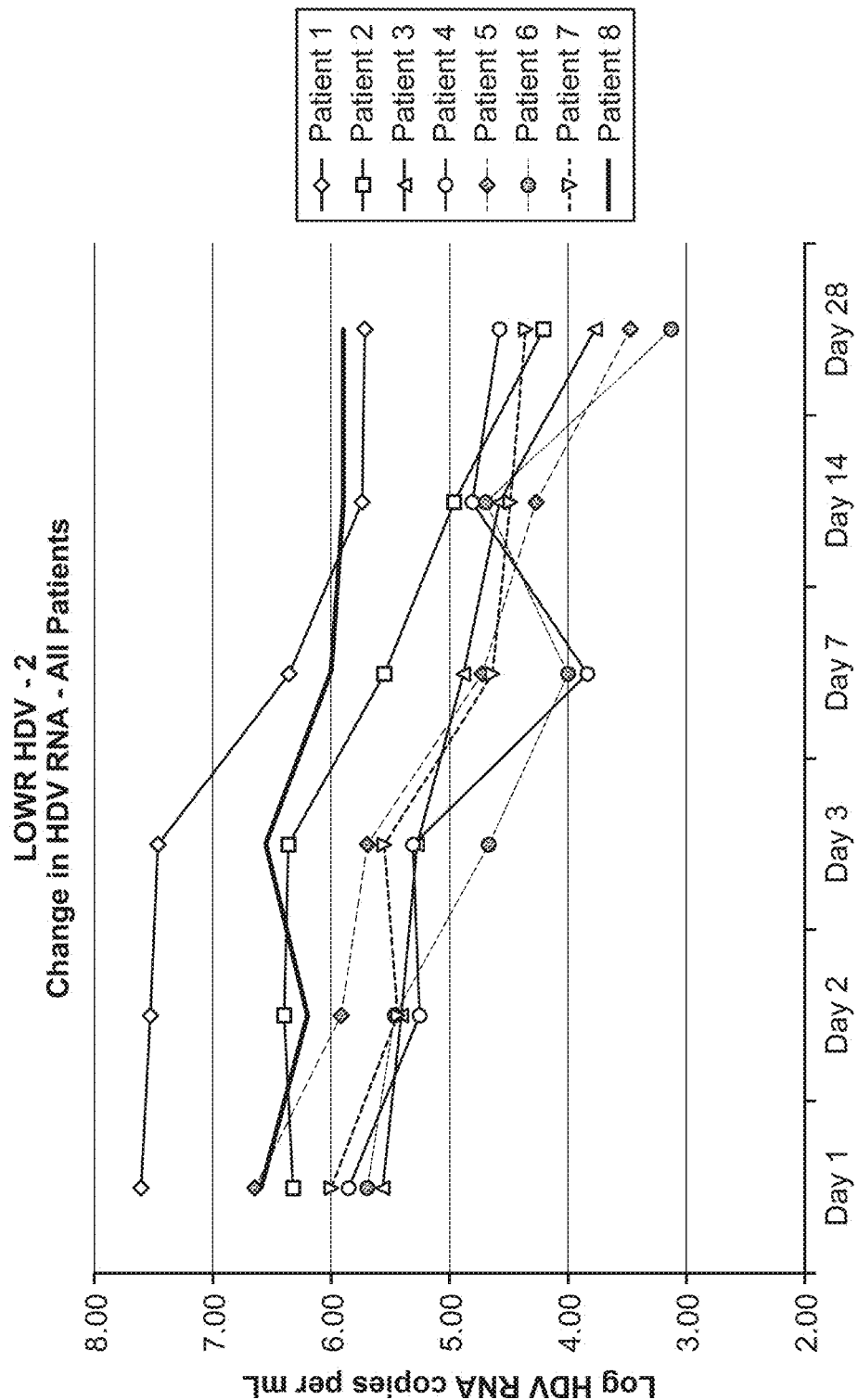
FIG. 4A-B. Changes in HDV-RNA viral titers after treatment with lonafarnib and ritonavir. Changes in HDV-RNA viral titers (A), and changes in HDV-RNA viral titers relative to a normalized baseline (B), in patients treated with separately formulated lonafarnib and ritonavir at doses described in Example 3.
Figure 4B:
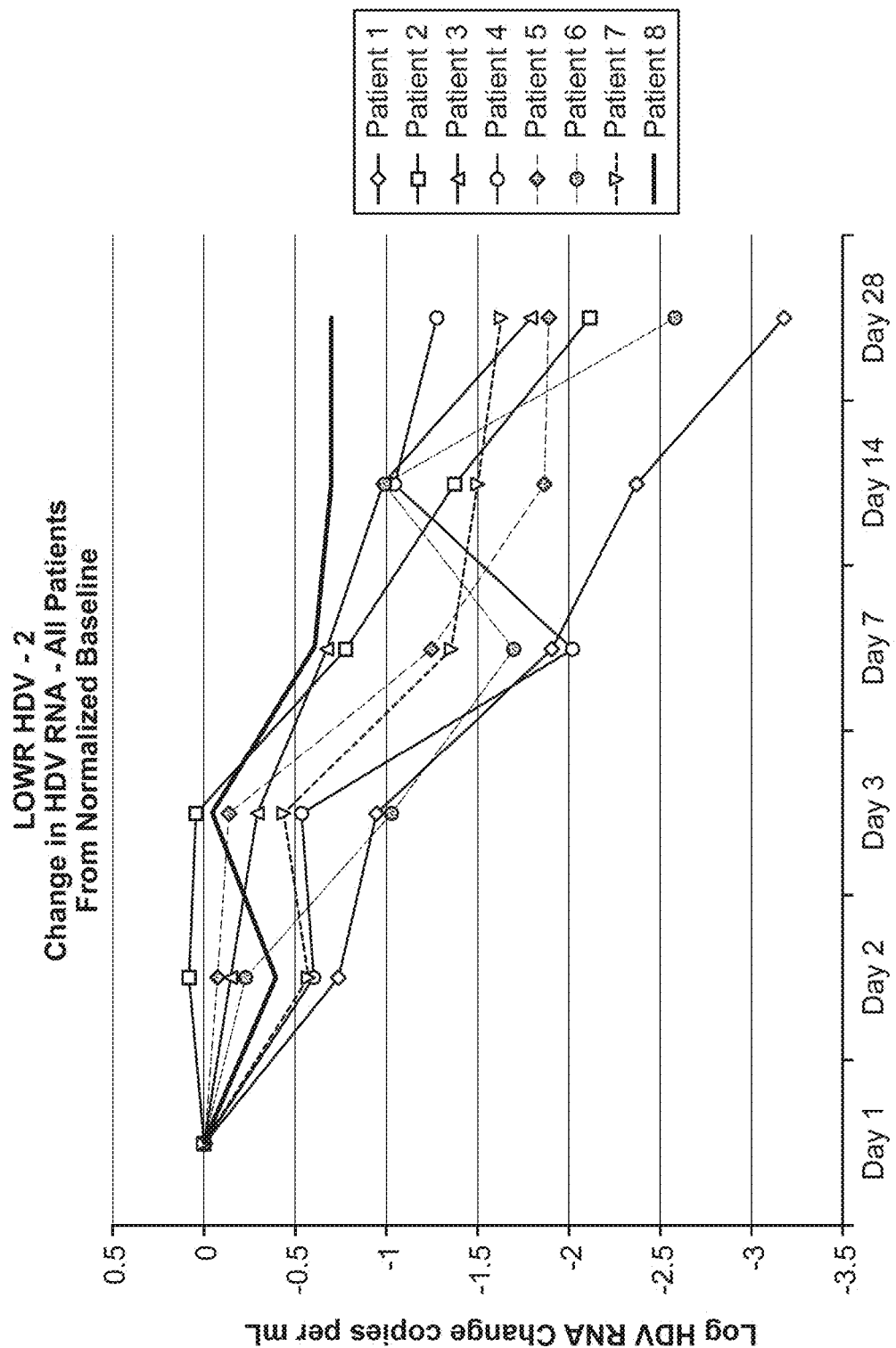

Time courses showing changes in HDV-RNA levels in patients 1-8 through 28 days are shown in FIG. 4A (showing HDV RNA levels) and FIG. 4B (change relative to a normalized baseline). The mean log viral load decline is 2 logs after 9-10 weeks. Nadirs are reached between week 4 to 6, after which VL plateaus or in some cases, elevate slightly. Group 3 may have reached a saturable absorption point, which suggests a lower lonafarnib dose is preferred.

Groups 1 and 4 maintained the highest C min. These two groups have either BID lonafarnib (Group 1) or BID ritonavir (Group 4). This suggests higher or more frequent ritonavir doses may be beneficial, such as BID. FIG. 4 illustrates that QD dosing of ritonavir (as shown in the graph) provides LNF serum concentrations that are in the 2500-3500 ng/mL range. By increasing RTN dosing to BID patients may achieve higher LND serum concentrations >5000 ng/mL.

Figure 5:
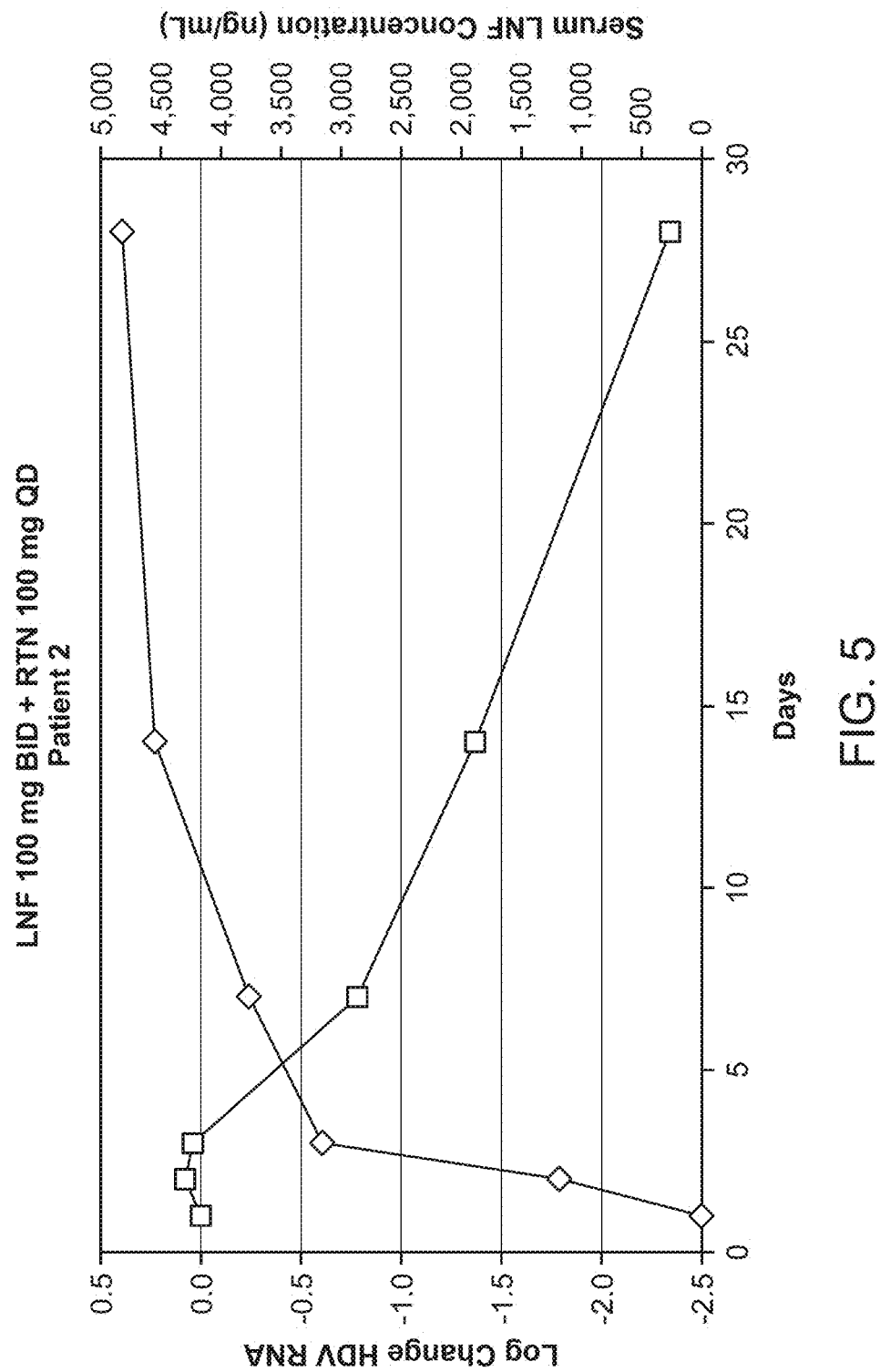
FIG. 5. Correlation between serum levels of lonafarnib and HDV-RNA virus levels in a patient treated with separately formulated 100 mg BID lonafarnib and 100 mg QD ritonavir as described in Example 3. There is an inverse correlation between higher (~5,000 ng/mL) lonafarnib serum levels and HDV viral load.
Figure 6:
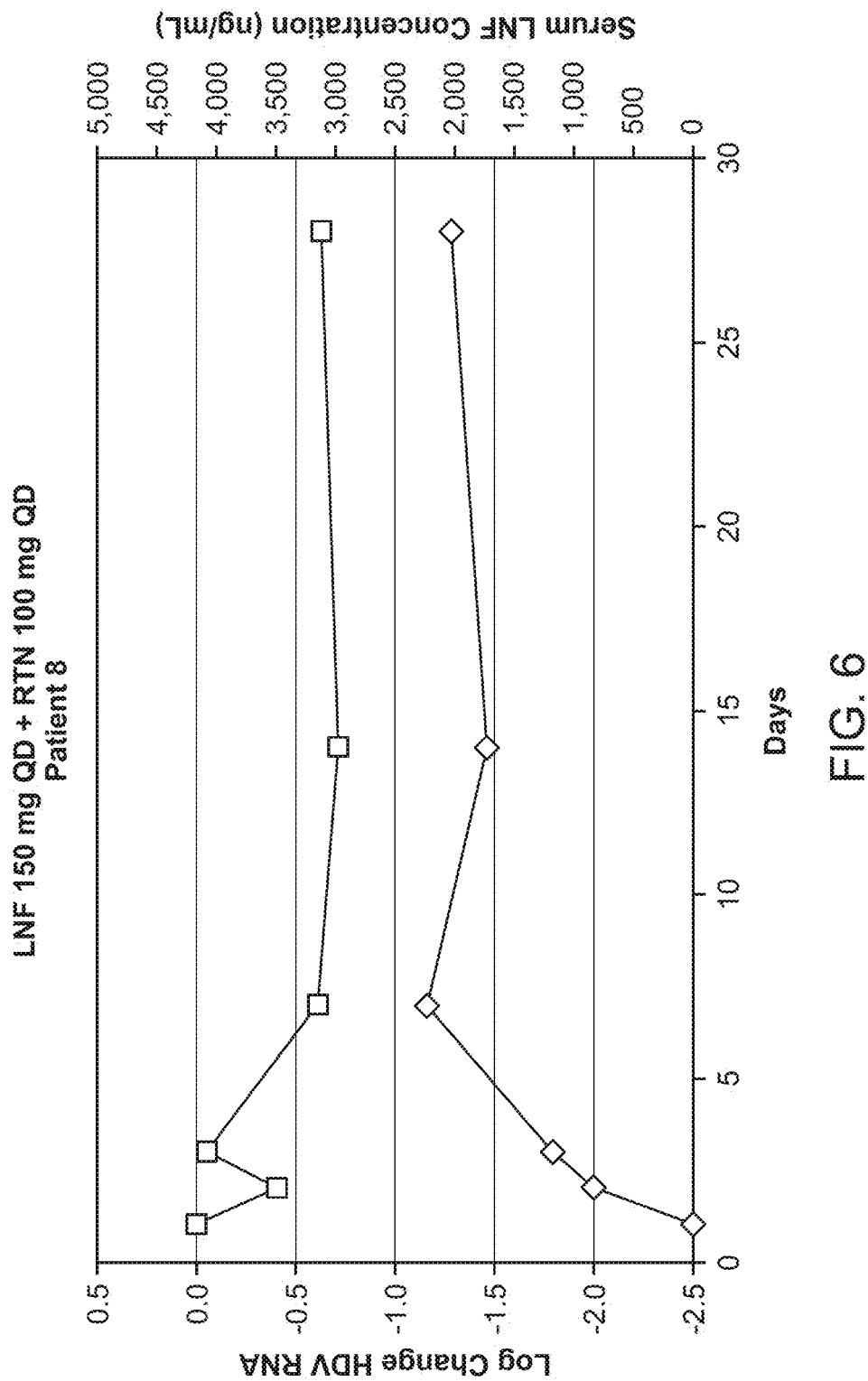
FIG. 6. A reduced correlation between lower (~2,000 ng/mL) lonafarnib serum levels and HDV viral load was observed in Patient 8 (see Example 3).
Figure 7:
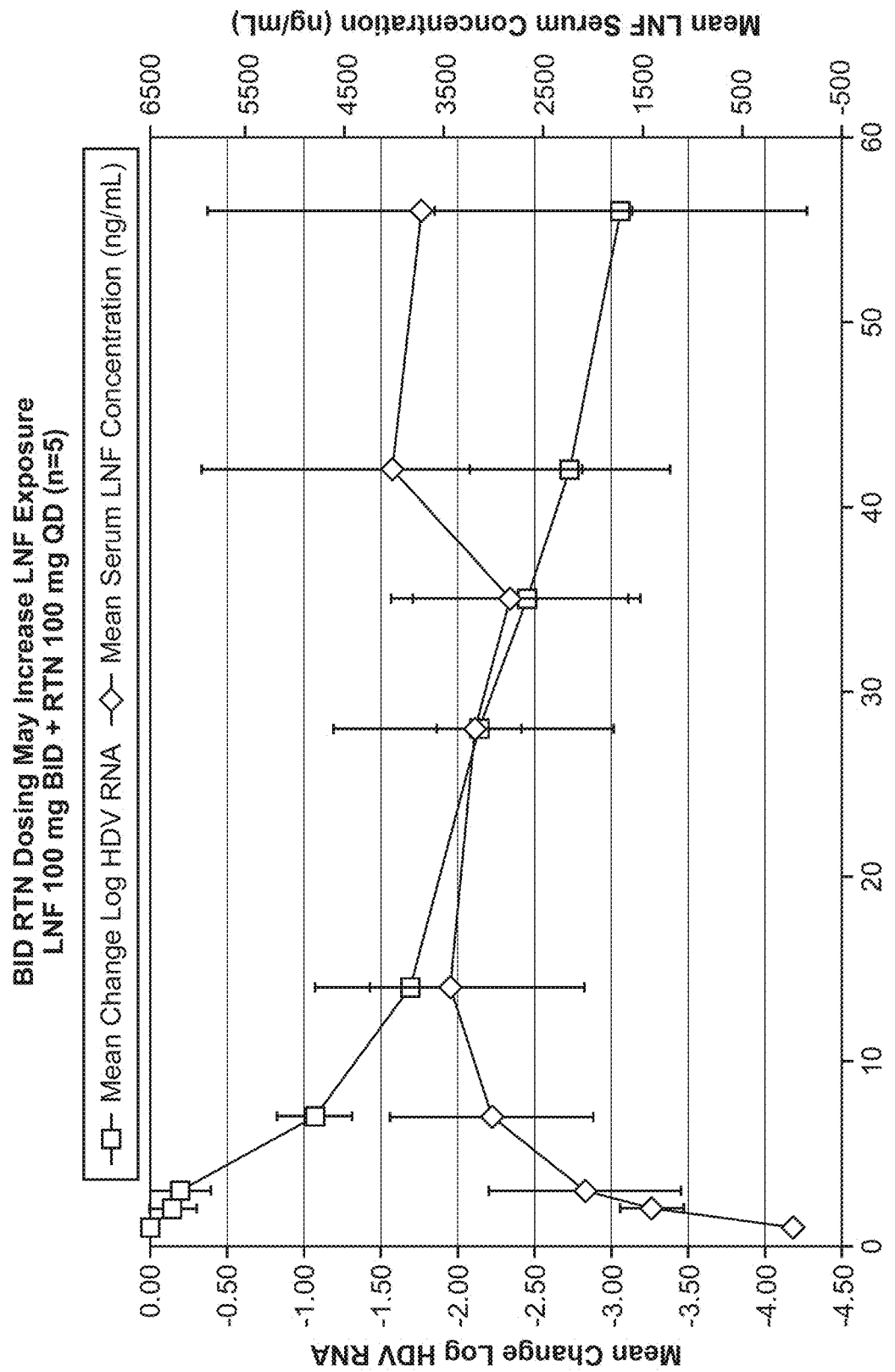
FIG. 7. Graphic illustration of the relationship between lonafarnib serum concentration and change in viral load over time for a 100 mg BID lonafarnib and 100 mg QD ritonavir dosing regimen (drugs separately formulated).

The results show that increasing serum levels of lonafarnib correlate with reducing levels of HDV-RNA in hepatitis delta infected patients. Some patients may not respond if serum lonafarnib levels fall below 2000 ng/mL, for example, as observed with patient 8 in FIG. 6. Lonafarnib levels approaching 5,000 ng/ml have the most profound effect on reducing HDV-RNA levels, as shown in FIG. 5.

Adverse Effects

Table 11 summarizes patients' adverse events during the first 6 weeks of therapy, and shows that 75% of patients in the study (six of eight patients) required at least one dose reduction in weeks 7-10.

TABLE 11

Lonafarnib Dose Reductions in Patients Experiencing Side Effects

| Patient | Lonafarnib Dose Reduction | Adverse events of LOWR2 patients during the course of the six week treatment |
|---|---|---|
| 1 | Dose reduction at "week 7" from 100 mg BID to 100 mg QD | Diarrhea and severe fatigue |
| 2 | Dose reduction at "week 7" from 100 mg BID to 50 mg (am) + 100 mg (pm) | Diarrhea. Fatigue and anorexia unbearable |
| 3 | Dose reduction at "week 8" from 100 mg BID to 150 QD | Diarrhea 2-3 times in a week (5-6 times per day), anorexia, fatigue |
| 4 | Dose reduction at "week 8" from 100 mg BID to 150 mg QD Further dose reduction at "week 10" from 150 mg QD to 50 mg QD | Severe anorexia, dry mouth, diarrhea 2-3 days per week |
| 5 | Dose reduction at "week 7" from 100 mg QD to 50 mg QD | Diarrhea 2 days per week, 3-4 bowel movements per day, anorexia and vomiting, fatigue |

TABLE 11-continued

Lonafarnib Dose Reductions in Patients Experiencing Side Effects

| Patient | Lonafarnib Dose Reduction | Adverse events of LOWR2 patients during the course of the six week treatment |
|---|---|---|
| 6 | — | nausea (moderate), diarrhea (rarely |
| 7 | — | Diarrhea continued (7-8 times per day), anorexia (moderate) |
| 8 | Dose reduction a "week 10" from 150 mg QD to 100 mg QD | Diarrhea 20 times per day, mild anorexia and nausea, severe fatigue |

Lonafarnib dose was reduced in 6 of 8 patients (patients 1, 2, 3, 4, 5, and 8) due to side effects. Dose reductions correlated with viral load plateau or increase. Lomotil and ondansetron were used by three of the eight patients (beginning at Week 4). Of the three patients, two did not require lonafarnib dose reduction. The present invention provides "low dose" lonafarnib (e.g., 25 mg, 50 mg, or 75 mg dose strengths) and ritonavir (e.g., 100 mg) coformulations that can be administered to patients sensitive to higher doses of lonafarnib.

In summary, the data show that therapy with separately-formulated lonafarnib and ritonavir is efficacious for treating patients infected with HDV. Administration of a unit dosage form comprising both lonafarnib and ritonavir as provided herein should be similarly efficacious for treating patient infected with HDV.

Example 4. Treatment of HDV Patients with 25 mg BID, 50 mg BID, or 75 mg BID Lonafarnib and 100 mg BID Ritonavir This example demonstrates the efficacy and tolerability of various combination regimens of separately formulated lonafarnib and ritonavir in patients infected with HDV. 38 patients were dosed as shown below in TABLE 12. The duration of treatment was 12-24 weeks. On day 1 and day 28 of treatment, a 72 hour PK and PD evaluation was performed. Additionally, during the course of treatment biochemical parameters and HDV RNA level (as measured by quantitative real-time PCR) were measured on days 1, 2, 3, 7, 14, and 28, and then every 4 weeks thereafter.

TABLE 12

Dosing regimen for lonafarnib-ritonavir cotherapy ± interferon

| Amount of lonafarnib | Amount of ritonavir | Amount of Pegylated interferon-α | Number of patients |
|---|---|---|---|
| 100 mg BID | 100 mg QD | — | 3 |
| 100 mg BID | 50 mg BID | — | 2 |
| 100 mg QD | 100 mg QD | — | 5 |
| 150 mg QD | 100 mg QD | — | 3 |
| 75 mg BID | 100 mg BID | — | 3 |
| 50 mg BID | 100 mg BID | — | 6 |
| 25 mg BID | 100 mg BID | — | 5 |
| 50 mg BID | 100 mg BID | 180 mcg QW | 3 |
| 25 mg BID | 100 mg BID | 180 mcg QW | 7 |

Figure 8:
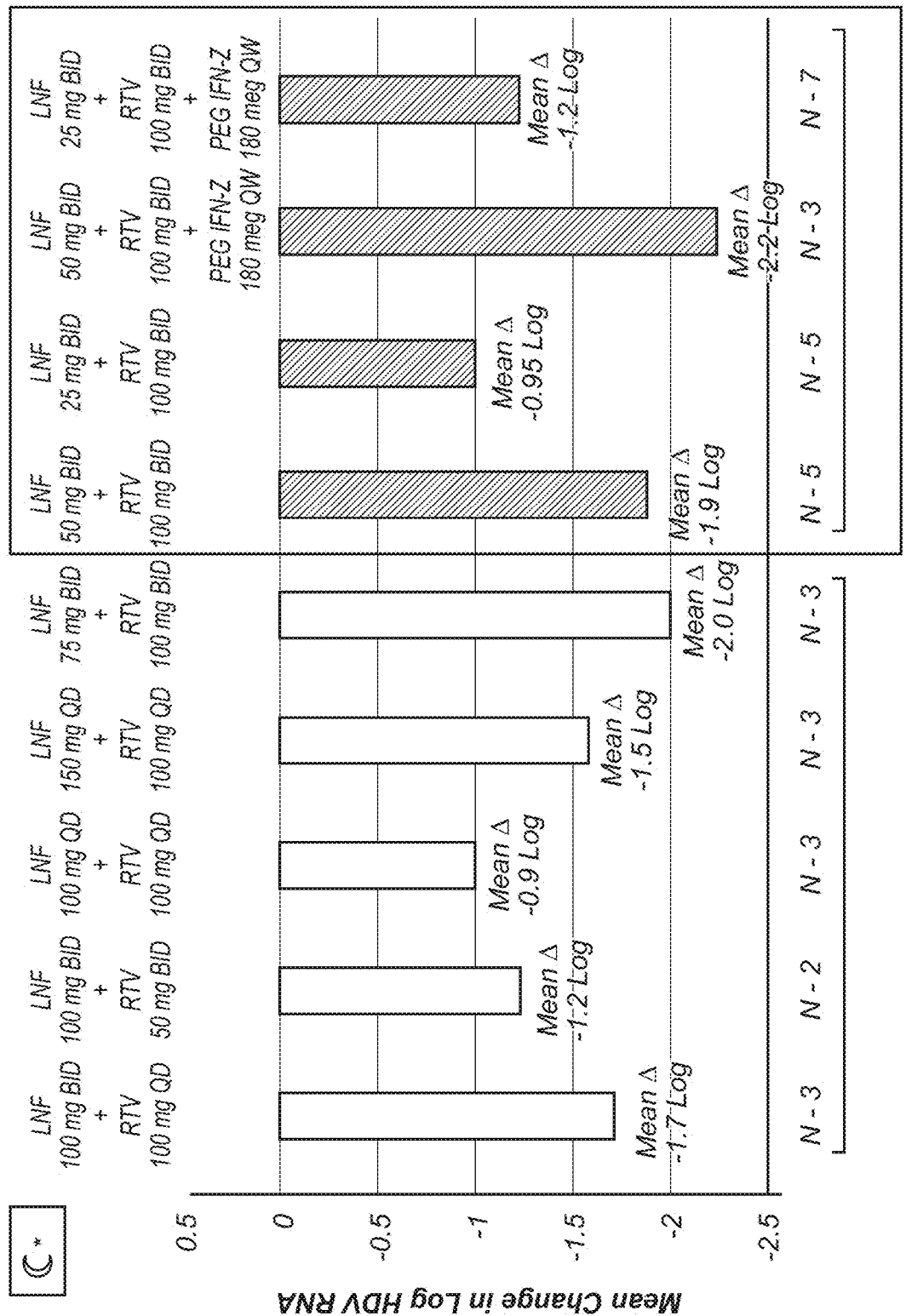
FIG. 8. Graphic illustration of changes in HDV RNA viral titers in patients treated with separately formulated lonafarnib and ritonavir as described in Example 4.

For all treatment groups, HDV RNA viral load was measured after 4 weeks of treatment and compared to baseline HDV RNA virus load. As shown in FIG. 8, comparable viral load decline was observed for patients receiving 75 mg BID lonafarnib+100 mg BID ritonavir, 50 mg BID lonafarnib+100 mg BID ritonavir, or 25 mg BID lonafarnib+100 mg BID ritonavir, as compared to patients receiving higher doses of lonafarnib in the lonafarnib-ritonavir co-therapy. Based on the data presented for separately administered lonafarnib and ritonavir, administration of a unit dosage form comprising both lonafarnib and ritonavir should be similarly efficacious for treating patient infected with HDV.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

What is claimed is:

1. A method of treating a hepatitis delta virus (HDV) infection in a human patient with an HDV infection, comprising:
    orally administering to the human patient a therapeutically effective amount of an amorphous co-precipitate comprising:
        lonafarnib or a pharmaceutically acceptable salt thereof; and
        ritonavir or a pharmaceutically acceptable salt thereof;
    wherein the amorphous co-precipitate is substantially free of crystalline forms, and
    wherein the amorphous co-precipitate is administered at a daily dose of lonafarnib of 50 mg to 200 mg once daily or twice daily.

2. The method of claim 1, wherein the lonafarnib or the pharmaceutically acceptable salt thereof and the ritonavir or the pharmaceutically acceptable salt thereof are present in the amorphous co-precipitate in a ratio of 0.5:1 to 2:1 (w/w).

3. The method of claim 1, wherein the amorphous co-precipitate is administered once daily.

4. The method of claim 1, wherein the human patient is treated with the amorphous co-precipitate for at least 30 days, at least 60 days, at least 90 days, at least 120 days, at least 150 days, or at least 180 days.

5. The method of claim 1, wherein the human patient is treated with the amorphous co-precipitate for rest of life of the human patient or until the administering is no longer effective in maintaining HDV at a sufficiently low level to provide meaningful therapeutic benefit.

6. The method of claim 1, further comprising administering to the human patient a gastrointestinal modifying agent.

7. The method of claim 1, wherein the amorphous co-precipitate is formulated as a tablet, caplet, gelcap, or a capsule.

8. The method of claim 1, wherein the HDV infection is a chronic HDV infection.

9. A method of treating a hepatitis delta virus (HDV) infection in a human patient with an HDV infection, comprising:
    orally administering to the human patient a therapeutically effective amount of an amorphous co-precipitate comprising:
        lonafarnib or a pharmaceutically acceptable salt thereof; and
        ritonavir or a pharmaceutically acceptable salt thereof;
    wherein the amorphous co-precipitate is substantially free of crystalline forms, and
    wherein the amorphous co-precipitate is administered once daily or twice daily.

10. The method of claim 9, wherein the amorphous co-precipitate administered to the human patient comprises the lonafarnib or the pharmaceutically acceptable salt thereof in an amount from about 20 mg to about 100 mg.

11. The method of claim 9, wherein the amorphous co-precipitate is administered once daily.

12. The method of claim 9, wherein the human patient is treated with the amorphous co-precipitate for at least 30 days, at least 60 days, at least 90 days, at least 120 days, at least 150 days, or at least 180 days.

13. The method of claim 9, wherein the human patient is treated with the amorphous co-precipitate for rest of life of the human patient or until the administering is no longer effective in maintaining HDV at a sufficiently low level to provide meaningful therapeutic benefit.

14. The method of claim 9, further comprising administering to the human patient a gastrointestinal modifying agent.

15. The method of claim 9, wherein the amorphous precipitate is formulated as a tablet, a caplet, a gelcap, or a capsule.

16. The method of claim 9, wherein the HDV infection is a chronic HDV infection.

17. A composition comprising an amorphous co-precipitate comprising: lonafarnib or a pharmaceutically acceptable salt thereof; ritonavir or a pharmaceutically acceptable salt thereof; and a co-polymer;
   wherein the amorphous co-precipitate is substantially free of crystalline forms,
   wherein the composition is formulated for oral administration, and
   wherein the composition comprises the lonafarnib or the pharmaceutically acceptable salt thereof in an amount from about 20 mg to about 100 mg.

18. The composition of claim 17, wherein the composition is formulated as a tablet, caplet, gelcap, or a capsule.

19. A unit dosage form comprising a composition of claim 17.

20. A unit dosage form comprising a composition of claim 17, wherein the unit dosage form is formulated as a tablet, a caplet, a gelcap, or a capsule.

* * * * *